United States Patent
Mai et al.

(10) Patent No.: US 10,166,003 B2
(45) Date of Patent: Jan. 1, 2019

(54) ULTRASOUND IMAGING WITH VARIABLE LINE DENSITY

(71) Applicant: VOLCANO CORPORATION, San Diego, CA (US)

(72) Inventors: Jerome Mai, West Sacramento, CA (US); Andrew Hancock, Sacramento, CA (US)

(73) Assignee: VOLCANO CORPORATION, San Diego, CA (US)

( * ) Notice: Subject to any disclaimer, the term of this patent is extended or adjusted under 35 U.S.C. 154(b) by 458 days.

(21) Appl. No.: 14/107,514

(22) Filed: Dec. 16, 2013

(65) Prior Publication Data
US 2014/0180107 A1    Jun. 26, 2014

Related U.S. Application Data

(60) Provisional application No. 61/745,025, filed on Dec. 21, 2012.

(51) Int. Cl.
*A61B 8/00* (2006.01)
*A61B 8/12* (2006.01)
(Continued)

(52) U.S. Cl.
CPC .......... *A61B 8/4461* (2013.01); *A61B 8/0891* (2013.01); *A61B 8/12* (2013.01);
(Continued)

(58) Field of Classification Search
CPC ....... A61B 8/4461; A61B 8/0891; A61B 8/54; A61B 8/445; G01S 7/52085;
(Continued)

(56) References Cited

U.S. PATENT DOCUMENTS 3,301,258 A   1/1967  Werner
3,617,880 A   11/1971 Cormack et al.
(Continued)

FOREIGN PATENT DOCUMENTS

EP   1041373 A2   10/2000
EP   01172637 A1  1/2002
(Continued)

OTHER PUBLICATIONS

International Search Report and Written Opinion dated Nov. 2, 2012, for International Patent Application No. PCT/US12/53168, filed Aug. 30, 2013 (8 pages).

(Continued)

*Primary Examiner* — Angela M Hoffa

(57) ABSTRACT

The invention generally relates to intravascular ultrasound imaging and to systems and methods to improve line density and image quality. The invention provides an intravascular imaging system that uses a clock device to provide a set of trigger signals for each revolution of the imaging catheter and capture various patterns of scan lines for each set of trigger signals. The system can be operated to capture two scan lines of data for each trigger signal thereby doubling scan line density compared to existing systems. The clock device can be provided by hardware, such as a rotary encoder, that is configured to define a maximum number of trigger signals that the module can provide per rotation of the catheter.

16 Claims, 13 Drawing Sheets

(51) Int. Cl.
*A61B 8/08* (2006.01)
*G01S 15/89* (2006.01)
*G01S 7/52* (2006.01)
*A61B 8/06* (2006.01)

(52) U.S. Cl.
CPC ............... *A61B 8/445* (2013.01); *A61B 8/54* (2013.01); *G01S 7/52085* (2013.01); *G01S 15/8934* (2013.01); *A61B 8/06* (2013.01); *A61B 8/4422* (2013.01); *A61B 8/46* (2013.01); *G01S 7/52082* (2013.01); *G01S 7/52084* (2013.01)

(58) Field of Classification Search
CPC ............. G01S 7/52088; G01S 7/52087; G01S 15/8934; G01S 7/52082; G01S 7/52084
See application file for complete search history.

(56) References Cited

U.S. PATENT DOCUMENTS

| | | |
|---|---|---|
| 3,789,841 A | 2/1974 | Antoshkiw |
| 3,841,308 A | 10/1974 | Tate |
| 4,140,364 A | 2/1979 | Yamashita et al. |
| 4,274,423 A | 6/1981 | Mizuno et al. |
| 4,344,438 A | 8/1982 | Schultz |
| 4,398,791 A | 8/1983 | Dorsey |
| 4,432,370 A | 2/1984 | Hughes et al. |
| 4,552,554 A | 11/1985 | Gould et al. |
| 4,577,543 A | 3/1986 | Wilson |
| 4,676,980 A | 6/1987 | Segal et al. |
| 4,682,895 A | 7/1987 | Costello |
| 4,733,665 A | 3/1988 | Palmaz |
| 4,744,619 A | 5/1988 | Cameron |
| 4,762,129 A | 8/1988 | Bonzel |
| 4,766,386 A | 8/1988 | Oliver et al. |
| 4,771,774 A | 9/1988 | Simpson et al. |
| 4,794,931 A | 1/1989 | Yock |
| 4,800,886 A | 1/1989 | Nestor |
| 4,803,639 A | 2/1989 | Steele et al. |
| 4,816,567 A | 3/1989 | Cabilly et al. |
| 4,819,740 A | 4/1989 | Warrington |
| 4,821,731 A | 4/1989 | Martinelli et al. |
| 4,824,435 A | 4/1989 | Giesy et al. |
| 4,830,023 A | 5/1989 | de Toledo et al. |
| 4,834,093 A | 5/1989 | Littleford et al. |
| 4,841,977 A | 6/1989 | Griffith et al. |
| 4,864,578 A | 9/1989 | Proffitt et al. |
| 4,873,690 A | 10/1989 | Adams |
| 4,877,314 A | 10/1989 | Kanamori |
| 4,887,606 A | 12/1989 | Yock et al. |
| 4,917,085 A | 4/1990 | Smith |
| 4,917,097 A | 4/1990 | Proudian et al. |
| 4,928,693 A | 5/1990 | Goodin et al. |
| 4,932,413 A | 6/1990 | Shockey et al. |
| 4,932,419 A | 6/1990 | de Toledo |
| 4,948,229 A | 8/1990 | Soref |
| 4,951,677 A | 8/1990 | Crowley et al. |
| 4,969,742 A | 11/1990 | Falk et al. |
| 4,987,412 A | 1/1991 | Vaitekunas et al. |
| 4,993,412 A | 2/1991 | Murphy-Chutorian |
| 4,998,972 A | 3/1991 | Chin et al. |
| 5,000,185 A | 3/1991 | Yock |
| 5,024,234 A | 6/1991 | Leary et al. |
| 5,025,445 A | 6/1991 | Anderson et al. |
| 5,032,123 A | 7/1991 | Katz et al. |
| 5,037,169 A | 8/1991 | Chun |
| 5,039,193 A | 8/1991 | Snow et al. |
| 5,040,548 A | 8/1991 | Yock |
| 5,041,108 A | 8/1991 | Fox et al. |
| 5,054,470 A | 10/1991 | Fry et al. |
| 5,054,492 A | 10/1991 | Scribner et al. |
| 5,065,010 A | 11/1991 | Knute |
| 5,065,769 A | 11/1991 | de Toledo |
| 5,085,221 A | 2/1992 | Ingebrigtsen et al. |
| 5,095,911 A | 3/1992 | Pomeranz |
| 5,100,424 A | 3/1992 | Jang et al. |
| 5,120,308 A | 6/1992 | Hess |
| 5,125,137 A | 6/1992 | Corl et al. |
| 5,125,410 A * | 6/1992 | Misono ............... A61B 8/06 128/908 |
| 5,131,393 A | 7/1992 | Ishiguro |
| 5,135,486 A | 8/1992 | Eberle et al. |
| 5,135,516 A | 8/1992 | Sahatjian et al. |
| 5,155,439 A | 10/1992 | Holmbo et al. |
| 5,158,548 A | 10/1992 | Lau et al. |
| 5,163,445 A | 11/1992 | Christian et al. |
| 5,167,233 A | 12/1992 | Eberle et al. |
| 5,174,295 A | 12/1992 | Christian et al. |
| 5,176,141 A | 1/1993 | Bom et al. |
| 5,176,674 A | 1/1993 | Hofmann |
| 5,178,159 A | 1/1993 | Christian |
| 5,183,048 A | 2/1993 | Eberle |
| 5,188,632 A | 2/1993 | Goldenberg |
| 5,201,316 A | 4/1993 | Pomeranz et al. |
| 5,202,745 A | 4/1993 | Sorin et al. |
| 5,203,779 A | 4/1993 | Muller et al. |
| 5,220,922 A | 6/1993 | Barany |
| 5,224,953 A | 7/1993 | Morgentaler |
| 5,226,421 A | 7/1993 | Frisbie et al. |
| 5,240,003 A | 8/1993 | Lancee et al. |
| 5,240,437 A | 8/1993 | Christian |
| 5,242,460 A | 9/1993 | Klein et al. |
| 5,243,988 A | 9/1993 | Sieben et al. |
| 5,257,974 A | 11/1993 | Cox |
| 5,266,302 A | 11/1993 | Peyman et al. |
| 5,267,954 A | 12/1993 | Nita |
| 5,301,001 A | 4/1994 | Murphy et al. |
| 5,312,425 A | 5/1994 | Evans et al. |
| 5,313,949 A | 5/1994 | Yock |
| 5,313,957 A | 5/1994 | Little |
| 5,319,492 A | 6/1994 | Dorn et al. |
| 5,321,501 A | 6/1994 | Swanson et al. |
| 5,325,198 A | 6/1994 | Hartley et al. |
| 5,336,178 A | 8/1994 | Kaplan et al. |
| 5,346,689 A | 9/1994 | Peyman et al. |
| 5,348,017 A | 9/1994 | Thornton et al. |
| 5,348,481 A | 9/1994 | Ortiz |
| 5,353,798 A | 10/1994 | Sieben |
| 5,358,409 A | 10/1994 | Obara |
| 5,358,478 A | 10/1994 | Thompson et al. |
| 5,368,037 A | 11/1994 | Eberle et al. |
| 5,373,845 A | 12/1994 | Gardineer et al. |
| 5,373,849 A | 12/1994 | Maroney et al. |
| 5,375,602 A | 12/1994 | Lancee et al. |
| 5,377,682 A | 1/1995 | Ueno et al. |
| 5,383,853 A | 1/1995 | Jung et al. |
| 5,387,193 A | 2/1995 | Miraki |
| 5,396,328 A | 3/1995 | Jestel et al. |
| 5,397,355 A | 3/1995 | Marin et al. |
| 5,405,377 A | 4/1995 | Cragg |
| 5,411,016 A | 5/1995 | Kume et al. |
| 5,417,216 A * | 5/1995 | Tanaka ............... A61B 8/12 600/446 |
| 5,419,777 A | 5/1995 | Hofling |
| 5,421,338 A | 6/1995 | Crowley et al. |
| 5,423,806 A | 6/1995 | Dale et al. |
| 5,427,118 A | 6/1995 | Nita et al. |
| 5,431,673 A | 7/1995 | Summers et al. |
| 5,436,759 A | 7/1995 | Dijaili et al. |
| 5,439,139 A | 8/1995 | Brovelli |
| 5,443,457 A | 8/1995 | Ginn et al. |
| 5,453,575 A | 9/1995 | O'Donnell et al. |
| 5,456,693 A | 10/1995 | Conston et al. |
| 5,459,570 A | 10/1995 | Swanson et al. |
| 5,480,388 A | 1/1996 | Zadini et al. |
| 5,485,845 A | 1/1996 | Verdonk et al. |
| 5,492,125 A | 2/1996 | Kim et al. |
| 5,496,997 A | 3/1996 | Pope |
| 5,507,761 A | 4/1996 | Duer |
| 5,512,044 A | 4/1996 | Duer |
| 5,514,128 A | 5/1996 | Hillsman et al. |
| 5,529,674 A | 6/1996 | Hedgcoth |
| 5,541,730 A | 7/1996 | Chaney |

(56) References Cited

U.S. PATENT DOCUMENTS

| | | | |
|---|---|---|---|
| 5,546,717 A | | 8/1996 | Penczak et al. |
| 5,546,948 A | | 8/1996 | Hamm et al. |
| 5,565,332 A | | 10/1996 | Hoogenboom et al. |
| 5,573,520 A | | 11/1996 | Schwartz et al. |
| 5,581,638 A | | 12/1996 | Givens et al. |
| 5,586,054 A | | 12/1996 | Jensen et al. |
| 5,588,434 A | * | 12/1996 | Fujimoto ............. A61B 8/12 600/443 |
| 5,592,939 A | | 1/1997 | Martinelli |
| 5,596,079 A | | 1/1997 | Smith et al. |
| 5,598,844 A | | 2/1997 | Diaz et al. |
| 5,609,606 A | | 3/1997 | O'Boyle |
| 5,630,806 A | | 5/1997 | Inagaki et al. |
| 5,651,366 A | | 7/1997 | Liang et al. |
| 5,660,180 A | | 8/1997 | Malinowski et al. |
| 5,667,499 A | | 9/1997 | Welch et al. |
| 5,667,521 A | | 9/1997 | Keown |
| 5,671,748 A | * | 9/1997 | Itoi ............. A61B 1/00165 600/117 |
| 5,672,877 A | | 9/1997 | Liebig et al. |
| 5,674,232 A | | 10/1997 | Halliburton |
| 5,693,015 A | | 12/1997 | Walker et al. |
| 5,713,848 A | | 2/1998 | Dubrul et al. |
| 5,745,634 A | | 4/1998 | Garrett et al. |
| 5,771,895 A | | 6/1998 | Slager |
| 5,779,731 A | | 7/1998 | Leavitt |
| 5,780,958 A | | 7/1998 | Strugach et al. |
| 5,798,521 A | | 8/1998 | Froggatt |
| 5,800,450 A | | 9/1998 | Lary et al. |
| 5,803,083 A | | 9/1998 | Buck et al. |
| 5,814,061 A | | 9/1998 | Osborne et al. |
| 5,817,025 A | | 10/1998 | Alekseev et al. |
| 5,820,594 A | | 10/1998 | Fontirroche et al. |
| 5,824,520 A | | 10/1998 | Mulligan-Kehoe |
| 5,827,313 A | | 10/1998 | Ream |
| 5,830,222 A | | 11/1998 | Makower |
| 5,848,121 A | | 12/1998 | Gupta et al. |
| 5,851,464 A | | 12/1998 | Davila et al. |
| 5,857,974 A | | 1/1999 | Eberle et al. |
| 5,872,829 A | | 2/1999 | Wischmann et al. |
| 5,873,835 A | | 2/1999 | Hastings et al. |
| 5,882,722 A | | 3/1999 | Kydd |
| 5,912,764 A | | 6/1999 | Togino |
| 5,916,194 A | | 6/1999 | Jacobsen et al. |
| 5,921,931 A | | 7/1999 | O'Donnell et al. |
| 5,925,055 A | | 7/1999 | Adrian et al. |
| 5,949,929 A | | 9/1999 | Hamm |
| 5,951,586 A | | 9/1999 | Berg et al. |
| 5,974,521 A | | 10/1999 | Akerib |
| 5,976,120 A | | 11/1999 | Chow et al. |
| 5,978,391 A | | 11/1999 | Das et al. |
| 5,997,523 A | | 12/1999 | Jang |
| 6,021,240 A | | 2/2000 | Murphy et al. |
| 6,022,319 A | | 2/2000 | Willard et al. |
| 6,031,071 A | | 2/2000 | Mandeville et al. |
| 6,036,889 A | | 3/2000 | Kydd |
| 6,039,690 A | * | 3/2000 | Holley ............. A61B 8/14 600/440 |
| 6,043,883 A | | 3/2000 | Leckel et al. |
| 6,045,505 A | | 4/2000 | Holley et al. |
| 6,050,944 A | | 4/2000 | Holley et al. |
| 6,050,949 A | | 4/2000 | White et al. |
| 6,059,738 A | | 5/2000 | Stoltze et al. |
| 6,068,638 A | | 5/2000 | Makower |
| 6,074,362 A | | 6/2000 | Jang et al. |
| 6,078,831 A | | 6/2000 | Belef et al. |
| 6,080,109 A | | 6/2000 | Baker et al. |
| 6,091,496 A | | 7/2000 | Hill |
| 6,094,591 A | | 7/2000 | Foltz et al. |
| 6,095,976 A | | 8/2000 | Nachtomy et al. |
| 6,097,755 A | | 8/2000 | Guenther, Jr. et al. |
| 6,099,471 A | | 8/2000 | Torp et al. |
| 6,099,549 A | | 8/2000 | Bosma et al. |
| 6,102,938 A | | 8/2000 | Evans et al. |
| 6,106,476 A | | 8/2000 | Corl et al. |
| 6,120,445 A | | 9/2000 | Grunwald |
| 6,123,673 A | | 9/2000 | Eberle et al. |
| 6,134,003 A | | 10/2000 | Tearney et al. |
| 6,139,510 A | | 10/2000 | Palermo |
| 6,141,089 A | | 10/2000 | Thoma et al. |
| 6,146,328 A | | 11/2000 | Chiao et al. |
| 6,148,095 A | | 11/2000 | Prause et al. |
| 6,151,433 A | | 11/2000 | Dower et al. |
| 6,152,877 A | | 11/2000 | Masters |
| 6,152,878 A | | 11/2000 | Nachtomy et al. |
| 6,159,225 A | | 12/2000 | Makower |
| 6,165,127 A | | 12/2000 | Crowley |
| 6,176,842 B1 | | 1/2001 | Tachibana et al. |
| 6,179,809 B1 | | 1/2001 | Khairkhahan et al. |
| 6,186,949 B1 | | 2/2001 | Hatfield et al. |
| 6,190,353 B1 | | 2/2001 | Makower et al. |
| 6,200,266 B1 | | 3/2001 | Shokrollahi et al. |
| 6,200,268 B1 | | 3/2001 | Vince et al. |
| 6,203,537 B1 | | 3/2001 | Adrian |
| 6,208,415 B1 | | 3/2001 | De Boer et al. |
| 6,210,332 B1 | | 4/2001 | Chiao et al. |
| 6,210,339 B1 | | 4/2001 | Kiepen et al. |
| 6,212,308 B1 | | 4/2001 | Donald |
| 6,231,518 B1 | | 5/2001 | Grabek et al. |
| 6,245,066 B1 | | 6/2001 | Morgan et al. |
| 6,249,076 B1 | | 6/2001 | Madden et al. |
| 6,254,543 B1 | | 7/2001 | Grunwald et al. |
| 6,256,090 B1 | | 7/2001 | Chen et al. |
| 6,258,052 B1 | | 7/2001 | Milo |
| 6,261,246 B1 | | 7/2001 | Pantages et al. |
| 6,275,628 B1 | | 8/2001 | Jones et al. |
| 6,283,921 B1 | | 9/2001 | Nix et al. |
| 6,283,951 B1 | | 9/2001 | Flaherty et al. |
| 6,295,308 B1 | | 9/2001 | Zah |
| 6,299,622 B1 | | 10/2001 | Snow et al. |
| 6,312,384 B1 | | 11/2001 | Chiao |
| 6,325,797 B1 | | 12/2001 | Stewart et al. |
| 6,328,696 B1 | | 12/2001 | Fraser |
| 6,343,168 B1 | | 1/2002 | Murphy et al. |
| 6,343,178 B1 | | 1/2002 | Burns et al. |
| 6,350,240 B1 | | 2/2002 | Song et al. |
| 6,354,997 B1 | | 3/2002 | Holley et al. |
| 6,364,841 B1 | | 4/2002 | White et al. |
| 6,366,722 B1 | | 4/2002 | Murphy et al. |
| 6,367,984 B1 | | 4/2002 | Stephenson et al. |
| 6,373,970 B1 | | 4/2002 | Dong et al. |
| 6,375,615 B1 | | 4/2002 | Flaherty et al. |
| 6,375,618 B1 | | 4/2002 | Chiao et al. |
| 6,375,628 B1 | | 4/2002 | Zadno-Azizi et al. |
| 6,376,830 B1 | | 4/2002 | Froggatt et al. |
| 6,379,352 B1 | | 4/2002 | Reynolds et al. |
| 6,381,350 B1 | | 4/2002 | Klingensmith et al. |
| 6,387,124 B1 | | 5/2002 | Buscemi et al. |
| 6,396,976 B1 | | 5/2002 | Little et al. |
| 6,398,792 B1 | | 6/2002 | O'Connor |
| 6,417,948 B1 | | 7/2002 | Chowdhury et al. |
| 6,419,644 B1 | | 7/2002 | White et al. |
| 6,421,164 B2 | | 7/2002 | Tearney et al. |
| 6,423,012 B1 | | 7/2002 | Kato et al. |
| 6,426,796 B1 | | 7/2002 | Pulliam et al. |
| 6,428,041 B1 | | 8/2002 | Wohllebe et al. |
| 6,428,498 B2 | | 8/2002 | Uflacker |
| 6,429,421 B1 | | 8/2002 | Meller et al. |
| 6,440,077 B1 | | 8/2002 | Jung et al. |
| 6,443,903 B1 | | 9/2002 | White et al. |
| 6,450,964 B1 | | 9/2002 | Webler |
| 6,457,365 B1 | | 10/2002 | Stephens et al. |
| 6,459,844 B1 | | 10/2002 | Pan |
| 6,468,290 B1 | | 10/2002 | Weldon et al. |
| 6,475,149 B1 | | 11/2002 | Sumanaweera |
| 6,480,285 B1 | | 11/2002 | Hill |
| 6,491,631 B2 | | 12/2002 | Chiao et al. |
| 6,491,636 B2 | | 12/2002 | Chenal et al. |
| 6,501,551 B1 | | 12/2002 | Tearney et al. |
| 6,504,286 B1 | | 1/2003 | Porat et al. |
| 6,508,824 B1 | | 1/2003 | Flaherty et al. |
| 6,514,237 B1 | | 2/2003 | Maseda |
| 6,520,269 B2 | | 2/2003 | Geiger et al. |
| 6,520,677 B2 | | 2/2003 | Iizuka |

(56) References Cited

U.S. PATENT DOCUMENTS

| | | |
|---|---|---|
| 6,535,764 B2 | 3/2003 | Imran et al. |
| 6,538,778 B1 | 3/2003 | Leckel et al. |
| 6,544,217 B1 | 4/2003 | Gulachenski |
| 6,544,230 B1 | 4/2003 | Flaherty et al. |
| 6,545,760 B1 | 4/2003 | Froggatt et al. |
| 6,546,272 B1 | 4/2003 | MacKinnon et al. |
| 6,551,250 B2 | 4/2003 | Khalil |
| 6,566,648 B1 | 5/2003 | Froggatt |
| 6,570,894 B2 | 5/2003 | Anderson |
| 6,572,555 B2 | 6/2003 | White et al. |
| 6,579,311 B1 | 6/2003 | Makower |
| 6,584,335 B1 | 6/2003 | Haar et al. |
| 6,592,612 B1 | 7/2003 | Samson et al. |
| 6,594,448 B2 | 7/2003 | Herman et al. |
| 6,602,241 B2 | 8/2003 | Makower et al. |
| 6,611,322 B1 | 8/2003 | Nakayama et al. |
| 6,611,720 B2 | 8/2003 | Hata et al. |
| 6,612,992 B1 | 9/2003 | Hossack et al. |
| 6,615,062 B2 | 9/2003 | Ryan et al. |
| 6,615,072 B1 | 9/2003 | Izatt et al. |
| 6,621,562 B2 | 9/2003 | Durston |
| 6,631,284 B2 | 10/2003 | Nutt et al. |
| 6,638,227 B2 | 10/2003 | Bae |
| 6,645,152 B1 | 11/2003 | Jung et al. |
| 6,646,745 B2 | 11/2003 | Verma et al. |
| 6,655,386 B1 | 12/2003 | Makower et al. |
| 6,659,957 B1 | 12/2003 | Vardi et al. |
| 6,660,024 B1 | 12/2003 | Flaherty et al. |
| 6,663,565 B2 | 12/2003 | Kawagishi et al. |
| 6,665,456 B2 | 12/2003 | Dave et al. |
| 6,669,716 B1 | 12/2003 | Gilson et al. |
| 6,671,055 B1 | 12/2003 | Wavering et al. |
| 6,673,015 B1 | 1/2004 | Glover et al. |
| 6,673,064 B1 | 1/2004 | Rentrop |
| 6,685,648 B2 | 2/2004 | Flaherty et al. |
| 6,689,056 B1 | 2/2004 | Kilcoyne et al. |
| 6,689,144 B2 | 2/2004 | Gerberding |
| 6,696,173 B1 | 2/2004 | Naundorf et al. |
| 6,701,044 B2 | 3/2004 | Arbore et al. |
| 6,701,176 B1 | 3/2004 | Halperin et al. |
| 6,709,444 B1 | 3/2004 | Makower |
| 6,712,836 B1 | 3/2004 | Berg et al. |
| 6,714,703 B2 | 3/2004 | Lee et al. |
| 6,719,717 B1 | 4/2004 | Johnson et al. |
| 6,725,073 B1 | 4/2004 | Motamedi et al. |
| 6,726,677 B1 | 4/2004 | Flaherty et al. |
| 6,730,107 B2 | 5/2004 | Kelley et al. |
| 6,733,474 B2 | 5/2004 | Kusleika |
| 6,738,144 B1 | 5/2004 | Dogariu |
| 6,740,113 B2 | 5/2004 | Vrba |
| 6,746,464 B1 | 6/2004 | Makower |
| 6,780,157 B2 | 8/2004 | Stephens et al. |
| 6,795,188 B2 | 9/2004 | Ruck et al. |
| 6,795,196 B2 | 9/2004 | Funakawa |
| 6,798,522 B2 | 9/2004 | Stolte et al. |
| 6,822,798 B2 | 11/2004 | Wu et al. |
| 6,830,559 B2 | 12/2004 | Schock |
| 6,832,024 B2 | 12/2004 | Gerstenberger et al. |
| 6,842,639 B1 | 1/2005 | Winston et al. |
| 6,847,449 B2 | 1/2005 | Bashkansky et al. |
| 6,855,115 B2 | 2/2005 | Fonseca et al. |
| 6,856,138 B2 | 2/2005 | Bohley |
| 6,856,400 B1 | 2/2005 | Froggatt |
| 6,856,472 B2 | 2/2005 | Herman et al. |
| 6,860,867 B2 | 3/2005 | Seward et al. |
| 6,866,670 B2 | 3/2005 | Rabiner et al. |
| 6,878,113 B2 | 4/2005 | Miwa et al. |
| 6,886,411 B2 | 5/2005 | Kjellman et al. |
| 6,891,984 B2 | 5/2005 | Petersen et al. |
| 6,895,106 B2 | 5/2005 | Wang et al. |
| 6,898,337 B2 | 5/2005 | Averett et al. |
| 6,900,897 B2 | 5/2005 | Froggatt |
| 6,912,051 B2 | 6/2005 | Jensen |
| 6,916,329 B1 | 7/2005 | Zhao |
| 6,922,498 B2 | 7/2005 | Shah |
| 6,937,346 B2 | 8/2005 | Nebendahl et al. |
| 6,937,696 B1 | 8/2005 | Mostafavi |
| 6,943,939 B1 | 9/2005 | DiJaili et al. |
| 6,947,147 B2 | 9/2005 | Motamedi et al. |
| 6,947,787 B2 | 9/2005 | Webler |
| 6,949,094 B2 | 9/2005 | Yaron |
| 6,952,603 B2 | 10/2005 | Gerber et al. |
| 6,954,737 B2 | 10/2005 | Kalantar et al. |
| 6,958,042 B2 | 10/2005 | Honda |
| 6,961,123 B1 | 11/2005 | Wang et al. |
| 6,966,891 B2 | 11/2005 | Ookubo et al. |
| 6,969,293 B2 | 11/2005 | Thai |
| 6,969,395 B2 | 11/2005 | Eskuri |
| 6,985,234 B2 | 1/2006 | Anderson |
| 7,004,963 B2 | 2/2006 | Wang et al. |
| 7,006,231 B2 | 2/2006 | Ostrovsky et al. |
| 7,010,458 B2 | 3/2006 | Wilt |
| 7,024,025 B2 | 4/2006 | Sathyanarayana |
| 7,027,211 B1 | 4/2006 | Ruffa |
| 7,027,743 B1 | 4/2006 | Tucker et al. |
| 7,033,347 B2 | 4/2006 | Appling |
| 7,035,484 B2 | 4/2006 | Silberberg et al. |
| 7,037,269 B2 | 5/2006 | Nix et al. |
| 7,042,573 B2 | 5/2006 | Froggatt |
| 7,044,915 B2 | 5/2006 | White et al. |
| 7,044,964 B2 | 5/2006 | Jang et al. |
| 7,048,711 B2 | 5/2006 | Rosenman et al. |
| 7,049,306 B2 | 5/2006 | Konradi et al. |
| 7,058,239 B2 | 6/2006 | Singh et al. |
| 7,060,033 B2 | 6/2006 | White et al. |
| 7,060,421 B2 | 6/2006 | Naundorf et al. |
| 7,063,679 B2 | 6/2006 | Maguire et al. |
| 7,068,852 B2 | 6/2006 | Braica |
| 7,074,188 B2 | 7/2006 | Nair et al. |
| 7,095,493 B2 | 8/2006 | Harres |
| 7,110,119 B2 | 9/2006 | Maestle |
| 7,113,875 B2 | 9/2006 | Terashima et al. |
| 7,123,777 B2 | 10/2006 | Rondinelli et al. |
| 7,130,054 B2 | 10/2006 | Ostrovsky et al. |
| 7,139,440 B2 | 11/2006 | Rondinelli et al. |
| 7,153,299 B1 | 12/2006 | Tu et al. |
| 7,171,078 B2 | 1/2007 | Sasaki et al. |
| 7,175,597 B2 | 2/2007 | Vince et al. |
| 7,177,491 B2 | 2/2007 | Dave et al. |
| 7,190,464 B2 | 3/2007 | Alphonse |
| 7,215,802 B2 | 5/2007 | Klingensmith et al. |
| 7,218,811 B2 | 5/2007 | Shigenaga et al. |
| 7,236,812 B1 | 6/2007 | Ballerstadt et al. |
| 7,245,125 B2 | 7/2007 | Harer et al. |
| 7,245,789 B2 | 7/2007 | Bates et al. |
| 7,249,357 B2 | 7/2007 | Landman et al. |
| 7,255,678 B2 | 8/2007 | Mehi et al. |
| 7,291,146 B2 | 11/2007 | Steinke et al. |
| 7,292,715 B2 | 11/2007 | Furnish |
| 7,292,885 B2 | 11/2007 | Scott et al. |
| 7,294,124 B2 | 11/2007 | Eidenschink |
| 7,300,460 B2 | 11/2007 | Levine et al. |
| 7,335,161 B2 | 2/2008 | Von Arx et al. |
| 7,337,079 B2 | 2/2008 | Park et al. |
| 7,355,716 B2 | 4/2008 | de Boer et al. |
| 7,356,367 B2 | 4/2008 | Liang et al. |
| 7,358,921 B2 | 4/2008 | Snyder et al. |
| 7,359,062 B2 | 4/2008 | Chen et al. |
| 7,359,554 B2 | 4/2008 | Klingensmith et al. |
| 7,363,927 B2 | 4/2008 | Ravikumar |
| 7,366,376 B2 | 4/2008 | Shishkov et al. |
| 7,382,949 B2 | 6/2008 | Bouma et al. |
| 7,387,636 B2 | 6/2008 | Cohn et al. |
| 7,391,520 B2 | 6/2008 | Zhou et al. |
| 7,397,935 B2 | 7/2008 | Kimmel et al. |
| 7,399,095 B2 | 7/2008 | Rondinelli |
| 7,408,648 B2 | 8/2008 | Kleen et al. |
| 7,414,779 B2 | 8/2008 | Huber et al. |
| 7,440,087 B2 | 10/2008 | Froggatt et al. |
| 7,447,388 B2 | 11/2008 | Bates et al. |
| 7,449,821 B2 | 11/2008 | Dausch |
| 7,450,165 B2 | 11/2008 | Ahiska |
| RE40,608 E | 12/2008 | Glover et al. |
| 7,458,967 B2 | 12/2008 | Appling et al. |

(56) References Cited

U.S. PATENT DOCUMENTS

| | | |
|---|---|---|
| 7,463,362 B2 | 12/2008 | Lasker et al. |
| 7,463,759 B2 | 12/2008 | Klingensmith et al. |
| 7,491,226 B2 | 2/2009 | Palmaz et al. |
| 7,515,276 B2 | 4/2009 | Froggatt et al. |
| 7,527,594 B2 | 5/2009 | Vardi et al. |
| 7,534,251 B2 | 5/2009 | WasDyke |
| 7,535,797 B2 | 5/2009 | Peng et al. |
| 7,547,304 B2 | 6/2009 | Johnson |
| 7,564,949 B2 | 7/2009 | Sattler et al. |
| 7,577,471 B2 | 8/2009 | Camus et al. |
| 7,583,857 B2 | 9/2009 | Xu et al. |
| 7,603,165 B2 | 10/2009 | Townsend et al. |
| 7,612,773 B2 | 11/2009 | Magnin et al. |
| 7,633,627 B2 | 12/2009 | Choma et al. |
| 7,645,229 B2 | 1/2010 | Armstrong |
| 7,658,715 B2 | 2/2010 | Park et al. |
| 7,660,452 B2 | 2/2010 | Zwirn et al. |
| 7,660,492 B2 | 2/2010 | Bates et al. |
| 7,666,204 B2 | 2/2010 | Thornton et al. |
| 7,672,790 B2 | 3/2010 | McGraw et al. |
| 7,680,247 B2 | 3/2010 | Atzinger et al. |
| 7,684,991 B2 | 3/2010 | Stohr et al. |
| 7,711,413 B2 | 5/2010 | Feldman et al. |
| 7,720,322 B2 | 5/2010 | Prisco |
| 7,728,986 B2 | 6/2010 | Lasker et al. |
| 7,734,009 B2 | 6/2010 | Brunner et al. |
| 7,736,317 B2 | 6/2010 | Stephens et al. |
| 7,742,795 B2 | 6/2010 | Stone et al. |
| 7,743,189 B2 | 6/2010 | Brown et al. |
| 7,762,954 B2 | 7/2010 | Nix et al. |
| 7,766,896 B2 | 8/2010 | Kornkven Volk et al. |
| 7,773,792 B2 | 8/2010 | Kimmel et al. |
| 7,775,981 B1 | 8/2010 | Guracar et al. |
| 7,777,399 B2 | 8/2010 | Eidenschink et al. |
| 7,781,724 B2 | 8/2010 | Childers et al. |
| 7,783,337 B2 | 8/2010 | Feldman et al. |
| 7,787,127 B2 | 8/2010 | Galle et al. |
| 7,792,342 B2 | 9/2010 | Barbu et al. |
| 7,801,343 B2 | 9/2010 | Unal et al. |
| 7,801,590 B2 | 9/2010 | Feldman et al. |
| 7,813,609 B2 | 10/2010 | Petersen et al. |
| 7,831,081 B2 | 11/2010 | Li |
| 7,846,101 B2 | 12/2010 | Eberle et al. |
| 7,853,104 B2 | 12/2010 | Oota et al. |
| 7,853,316 B2 | 12/2010 | Milner et al. |
| 7,860,555 B2 | 12/2010 | Saadat |
| 7,862,508 B2 | 1/2011 | Davies et al. |
| 7,872,759 B2 | 1/2011 | Tearney et al. |
| 7,880,868 B2 | 2/2011 | Aoki |
| 7,881,763 B2 | 2/2011 | Brauker et al. |
| 7,909,844 B2 | 3/2011 | Alkhatib et al. |
| 7,921,854 B2 | 4/2011 | Hennings et al. |
| 7,927,784 B2 | 4/2011 | Simpson |
| 7,929,148 B2 | 4/2011 | Kemp |
| 7,930,014 B2 | 4/2011 | Huennekens et al. |
| 7,930,104 B2 | 4/2011 | Baker et al. |
| 7,936,462 B2 | 5/2011 | Jiang et al. |
| 7,942,852 B2 | 5/2011 | Mas et al. |
| 7,947,012 B2 | 5/2011 | Spurchise et al. |
| 7,951,186 B2 | 5/2011 | Eidenschink et al. |
| 7,952,719 B2 | 5/2011 | Brennan, III |
| 7,972,353 B2 | 7/2011 | Hendriksen et al. |
| 7,976,492 B2 | 7/2011 | Brauker et al. |
| 7,977,950 B2 | 7/2011 | Maslen |
| 7,978,916 B2 | 7/2011 | Klingensmith et al. |
| 7,981,041 B2 | 7/2011 | McGahan |
| 7,981,151 B2 | 7/2011 | Rowe |
| 7,983,737 B2 | 7/2011 | Feldman et al. |
| 7,993,333 B2 | 8/2011 | Oral et al. |
| 7,995,210 B2 | 8/2011 | Tearney et al. |
| 7,996,060 B2 | 8/2011 | Trofimov et al. |
| 7,999,938 B2 | 8/2011 | Wang |
| 8,021,377 B2 | 9/2011 | Eskuri |
| 8,021,420 B2 | 9/2011 | Dolan |
| 8,036,732 B2 | 10/2011 | Milner |
| 8,040,586 B2 | 10/2011 | Smith et al. |
| 8,047,996 B2 | 11/2011 | Goodnow et al. |
| 8,049,900 B2 | 11/2011 | Kemp et al. |
| 8,050,478 B2 | 11/2011 | Li et al. |
| 8,050,523 B2 | 11/2011 | Younge et al. |
| 8,052,605 B2 | 11/2011 | Muller et al. |
| 8,057,394 B2 | 11/2011 | Dala-Krishna |
| 8,059,923 B2 | 11/2011 | Bates et al. |
| 8,070,800 B2 | 12/2011 | Lock et al. |
| 8,080,800 B2 | 12/2011 | Hoctor et al. |
| 8,088,102 B2 | 1/2012 | Adams et al. |
| 8,100,838 B2 | 1/2012 | Wright et al. |
| 8,104,479 B2 | 1/2012 | Glynn et al. |
| 8,108,030 B2 | 1/2012 | Castella et al. |
| 8,114,102 B2 | 2/2012 | Galdonik et al. |
| 8,116,605 B2 | 2/2012 | Petersen et al. |
| 8,125,648 B2 | 2/2012 | Milner et al. |
| 8,126,239 B2 | 2/2012 | Sun et al. |
| 8,133,199 B2 | 3/2012 | Weber et al. |
| 8,133,269 B2 | 3/2012 | Flechsenhar et al. |
| 8,140,708 B2 | 3/2012 | Zaharia et al. |
| 8,148,877 B2 | 4/2012 | Jiang et al. |
| 8,167,932 B2 | 5/2012 | Bourang et al. |
| 8,172,757 B2 | 5/2012 | Jaffe et al. |
| 8,177,809 B2 | 5/2012 | Mavani et al. |
| 8,187,191 B2 | 5/2012 | Hancock et al. |
| 8,187,267 B2 | 5/2012 | Pappone et al. |
| 8,187,830 B2 | 5/2012 | Hu et al. |
| 8,199,218 B2 | 6/2012 | Lee et al. |
| 8,206,429 B2 | 6/2012 | Gregorich et al. |
| 8,208,995 B2 | 6/2012 | Tearney et al. |
| 8,214,010 B2 | 7/2012 | Courtney et al. |
| 8,222,906 B2 | 7/2012 | Wyar et al. |
| 8,233,681 B2 | 7/2012 | Aylward et al. |
| 8,233,718 B2 | 7/2012 | Klingensmith et al. |
| 8,238,624 B2 | 8/2012 | Doi et al. |
| 8,239,938 B2 | 8/2012 | Simeral et al. |
| 8,277,386 B2 | 10/2012 | Ahmed et al. |
| 8,280,470 B2 | 10/2012 | Milner et al. |
| 8,289,284 B2 | 10/2012 | Glynn et al. |
| 8,289,522 B2 | 10/2012 | Tearney et al. |
| 8,298,147 B2 | 10/2012 | Huennekens et al. |
| 8,298,149 B2 | 10/2012 | Hastings et al. |
| 8,301,000 B2 | 10/2012 | Sillard et al. |
| 8,309,428 B2 | 11/2012 | Lemmerhirt et al. |
| 8,317,713 B2 | 11/2012 | Davies et al. |
| 8,323,201 B2 | 12/2012 | Towfiq et al. |
| 8,329,053 B2 | 12/2012 | Martin et al. |
| 8,336,643 B2 | 12/2012 | Harleman |
| 8,349,000 B2 | 1/2013 | Schreck |
| 8,353,945 B2 | 1/2013 | Andreas et al. |
| 8,353,954 B2 | 1/2013 | Cai et al. |
| 8,357,981 B2 | 1/2013 | Martin et al. |
| 8,361,097 B2 | 1/2013 | Patel et al. |
| 8,386,560 B2 | 2/2013 | Ma et al. |
| 8,398,591 B2 | 3/2013 | Mas et al. |
| 8,403,856 B2 * | 3/2013 | Corl .................. A61B 8/12 600/437 |
| 8,412,312 B2 | 4/2013 | Judell et al. |
| 8,417,491 B2 | 4/2013 | Trovato et al. |
| 8,449,465 B2 | 5/2013 | Nair et al. |
| 8,454,685 B2 | 6/2013 | Hariton et al. |
| 8,454,686 B2 | 6/2013 | Alkhatib |
| 8,475,522 B2 | 7/2013 | Jimenez et al. |
| 8,478,384 B2 | 7/2013 | Schmitt et al. |
| 8,486,062 B2 | 7/2013 | Belhe et al. |
| 8,486,063 B2 | 7/2013 | Werneth et al. |
| 8,491,567 B2 | 7/2013 | Magnin et al. |
| 8,500,798 B2 | 8/2013 | Rowe et al. |
| 8,550,911 B2 | 10/2013 | Sylla |
| 8,594,757 B2 | 11/2013 | Boppart et al. |
| 8,597,349 B2 | 12/2013 | Alkhatib |
| 8,600,477 B2 | 12/2013 | Beyar et al. |
| 8,600,917 B1 | 12/2013 | Schimert et al. |
| 8,601,056 B2 | 12/2013 | Lauwers et al. |
| 8,620,055 B2 | 12/2013 | Barratt et al. |
| 8,644,910 B2 | 2/2014 | Rousso et al. |
| 8,712,506 B2 | 4/2014 | Courtney et al. |

(56) References Cited

U.S. PATENT DOCUMENTS

| | | |
|---|---|---|
| 8,961,425 B2 * | 2/2015 | Corl .............. A61B 8/12 600/407 |
| 2001/0007940 A1 | 7/2001 | Tu et al. |
| 2001/0029337 A1 | 10/2001 | Pantages et al. |
| 2001/0037073 A1 | 11/2001 | White et al. |
| 2001/0046345 A1 | 11/2001 | Snyder et al. |
| 2001/0049548 A1 | 12/2001 | Vardi et al. |
| 2002/0034276 A1 | 3/2002 | Hu et al. |
| 2002/0041723 A1 | 4/2002 | Ronnekleiv et al. |
| 2002/0069676 A1 | 6/2002 | Kopp, II et al. |
| 2002/0089335 A1 | 7/2002 | Williams |
| 2002/0099289 A1 | 7/2002 | Crowley |
| 2002/0163646 A1 | 11/2002 | Anderson |
| 2002/0186818 A1 | 12/2002 | Arnaud et al. |
| 2002/0196446 A1 | 12/2002 | Roth et al. |
| 2002/0197456 A1 | 12/2002 | Pope |
| 2003/0004412 A1 | 1/2003 | Izatt et al. |
| 2003/0016604 A1 | 1/2003 | Hanes |
| 2003/0018273 A1 | 1/2003 | Corl et al. |
| 2003/0023153 A1 | 1/2003 | Izatt et al. |
| 2003/0032886 A1 | 2/2003 | Dgany et al. |
| 2003/0050871 A1 | 3/2003 | Broughton |
| 2003/0065371 A1 | 4/2003 | Satake |
| 2003/0069723 A1 | 4/2003 | Hegde |
| 2003/0077043 A1 | 4/2003 | Hamm et al. |
| 2003/0085635 A1 | 5/2003 | Davidsen |
| 2003/0090753 A1 | 5/2003 | Takeyama et al. |
| 2003/0092995 A1 | 5/2003 | Thompson |
| 2003/0093059 A1 | 5/2003 | Griffin et al. |
| 2003/0103212 A1 | 6/2003 | Westphal et al. |
| 2003/0152259 A1 | 8/2003 | Belykh et al. |
| 2003/0181802 A1 | 9/2003 | Ogawa |
| 2003/0187369 A1 | 10/2003 | Lewis et al. |
| 2003/0194165 A1 | 10/2003 | Silberberg et al. |
| 2003/0195419 A1 | 10/2003 | Harada |
| 2003/0208116 A1 | 11/2003 | Liang et al. |
| 2003/0212491 A1 | 11/2003 | Mitchell et al. |
| 2003/0219202 A1 | 11/2003 | Loeb et al. |
| 2003/0220749 A1 | 11/2003 | Chen et al. |
| 2003/0228039 A1 | 12/2003 | Green |
| 2004/0015065 A1 | 1/2004 | Panescu et al. |
| 2004/0023317 A1 | 2/2004 | Motamedi et al. |
| 2004/0028333 A1 | 2/2004 | Lomas |
| 2004/0037742 A1 | 2/2004 | Jen et al. |
| 2004/0042066 A1 | 3/2004 | Kinoshita et al. |
| 2004/0054287 A1 | 3/2004 | Stephens |
| 2004/0067000 A1 | 4/2004 | Bates et al. |
| 2004/0068161 A1 | 4/2004 | Couvillon |
| 2004/0082844 A1 | 4/2004 | Vardi et al. |
| 2004/0092830 A1 | 5/2004 | Scott et al. |
| 2004/0106853 A1 | 6/2004 | Moriyama |
| 2004/0111552 A1 | 6/2004 | Arimilli et al. |
| 2004/0122319 A1 | 6/2004 | Mehi et al. |
| 2004/0126048 A1 | 7/2004 | Dave et al. |
| 2004/0143160 A1 | 7/2004 | Couvillon |
| 2004/0146546 A1 | 7/2004 | Gravett et al. |
| 2004/0186369 A1 | 9/2004 | Lam |
| 2004/0186558 A1 | 9/2004 | Pavcnik et al. |
| 2004/0195512 A1 | 10/2004 | Crosetto |
| 2004/0220606 A1 | 11/2004 | Goshgarian |
| 2004/0225220 A1 | 11/2004 | Rich |
| 2004/0239938 A1 | 12/2004 | Izatt |
| 2004/0242990 A1 | 12/2004 | Brister et al. |
| 2004/0248439 A1 | 12/2004 | Gernhardt et al. |
| 2004/0260236 A1 | 12/2004 | Manning et al. |
| 2005/0013778 A1 | 1/2005 | Green et al. |
| 2005/0031176 A1 | 2/2005 | Hertel et al. |
| 2005/0036150 A1 | 2/2005 | Izatt et al. |
| 2005/0078317 A1 | 4/2005 | Law et al. |
| 2005/0101859 A1 | 5/2005 | Maschke |
| 2005/0140582 A1 | 6/2005 | Lee et al. |
| 2005/0140682 A1 | 6/2005 | Sumanaweera et al. |
| 2005/0140981 A1 | 6/2005 | Waelti |
| 2005/0140984 A1 | 6/2005 | Hitzenberger |
| 2005/0147303 A1 | 7/2005 | Zhou et al. |
| 2005/0165439 A1 | 7/2005 | Weber et al. |
| 2005/0171433 A1 | 8/2005 | Boppart et al. |
| 2005/0171438 A1 | 8/2005 | Chen et al. |
| 2005/0182297 A1 | 8/2005 | Gravenstein et al. |
| 2005/0196028 A1 | 9/2005 | Kleen et al. |
| 2005/0197585 A1 | 9/2005 | Brockway et al. |
| 2005/0213103 A1 | 9/2005 | Everett et al. |
| 2005/0215942 A1 | 9/2005 | Abrahamson et al. |
| 2005/0234445 A1 | 10/2005 | Conquergood et al. |
| 2005/0243322 A1 | 11/2005 | Lasker et al. |
| 2005/0249391 A1 | 11/2005 | Kimmel et al. |
| 2005/0251567 A1 | 11/2005 | Ballew et al. |
| 2005/0254059 A1 | 11/2005 | Alphonse |
| 2005/0264823 A1 | 12/2005 | Zhu et al. |
| 2006/0013523 A1 | 1/2006 | Childlers et al. |
| 2006/0015126 A1 | 1/2006 | Sher |
| 2006/0029634 A1 | 2/2006 | Berg et al. |
| 2006/0036167 A1 | 2/2006 | Shina |
| 2006/0038115 A1 | 2/2006 | Maas |
| 2006/0039004 A1 | 2/2006 | de Boer et al. |
| 2006/0041180 A1 | 2/2006 | Viswanathan et al. |
| 2006/0045536 A1 | 3/2006 | Arahira |
| 2006/0055936 A1 | 3/2006 | Yun et al. |
| 2006/0058622 A1 | 3/2006 | Tearney et al. |
| 2006/0064009 A1 | 3/2006 | Webler et al. |
| 2006/0067620 A1 | 3/2006 | Shishkov et al. |
| 2006/0072808 A1 | 4/2006 | Grimm et al. |
| 2006/0074442 A1 | 4/2006 | Noriega et al. |
| 2006/0098927 A1 | 5/2006 | Schmidt et al. |
| 2006/0100694 A1 | 5/2006 | Globerman |
| 2006/0106375 A1 | 5/2006 | Werneth et al. |
| 2006/0132790 A1 | 6/2006 | Gutin |
| 2006/0135870 A1 | 6/2006 | Webler |
| 2006/0142703 A1 | 6/2006 | Carter et al. |
| 2006/0142733 A1 | 6/2006 | Forsberg |
| 2006/0173299 A1 | 8/2006 | Romley et al. |
| 2006/0179255 A1 | 8/2006 | Yamazaki |
| 2006/0184048 A1 | 8/2006 | Saadat |
| 2006/0187537 A1 | 8/2006 | Huber et al. |
| 2006/0195269 A1 | 8/2006 | Yeatman et al. |
| 2006/0204119 A1 | 9/2006 | Feng et al. |
| 2006/0229591 A1 | 10/2006 | Lee |
| 2006/0239312 A1 | 10/2006 | Kewitsch et al. |
| 2006/0241342 A1 | 10/2006 | Macaulay et al. |
| 2006/0241465 A1 | 10/2006 | Huennekens et al. |
| 2006/0241503 A1 | 10/2006 | Schmitt et al. |
| 2006/0244973 A1 | 11/2006 | Yun et al. |
| 2006/0258895 A1 | 11/2006 | Maschke |
| 2006/0264743 A1 | 11/2006 | Kleen et al. |
| 2006/0267756 A1 | 11/2006 | Kates |
| 2006/0270976 A1 | 11/2006 | Savage et al. |
| 2006/0276709 A1 | 12/2006 | Khamene et al. |
| 2006/0279742 A1 | 12/2006 | Tearney et al. |
| 2006/0279743 A1 | 12/2006 | Boesser et al. |
| 2006/0285638 A1 | 12/2006 | Boese et al. |
| 2006/0287595 A1 | 12/2006 | Maschke |
| 2006/0293597 A1 | 12/2006 | Johnson et al. |
| 2007/0015969 A1 | 1/2007 | Feldman et al. |
| 2007/0016029 A1 | 1/2007 | Donaldson et al. |
| 2007/0016034 A1 | 1/2007 | Donaldson |
| 2007/0016062 A1 | 1/2007 | Park et al. |
| 2007/0027390 A1 | 2/2007 | Maschke et al. |
| 2007/0036417 A1 | 2/2007 | Argiro et al. |
| 2007/0038061 A1 | 2/2007 | Huennekens et al. |
| 2007/0038121 A1 | 2/2007 | Feldman et al. |
| 2007/0038125 A1 | 2/2007 | Kleen et al. |
| 2007/0043292 A1 | 2/2007 | Camus et al. |
| 2007/0043597 A1 | 2/2007 | Donaldson |
| 2007/0049847 A1 | 3/2007 | Osborne |
| 2007/0060973 A1 | 3/2007 | Ludvig et al. |
| 2007/0065077 A1 | 3/2007 | Childers et al. |
| 2007/0066888 A1 | 3/2007 | Maschke |
| 2007/0066890 A1 | 3/2007 | Maschke |
| 2007/0066983 A1 | 3/2007 | Maschke |
| 2007/0084995 A1 | 4/2007 | Newton et al. |
| 2007/0100226 A1 | 5/2007 | Yankelevitz et al. |
| 2007/0135887 A1 | 6/2007 | Maschke |
| 2007/0142707 A1 | 6/2007 | Wiklof et al. |
| 2007/0156019 A1 | 7/2007 | Larkin et al. |

(56) References Cited

U.S. PATENT DOCUMENTS

| | | |
|---|---|---|
| 2007/0161893 A1 | 7/2007 | Milner et al. |
| 2007/0161896 A1 | 7/2007 | Adachi et al. |
| 2007/0161963 A1 | 7/2007 | Smalling |
| 2007/0162860 A1 | 7/2007 | Muralidharan et al. |
| 2007/0165141 A1 | 7/2007 | Srinivas et al. |
| 2007/0167710 A1 | 7/2007 | Unal et al. |
| 2007/0167804 A1 | 7/2007 | Park et al. |
| 2007/0191682 A1 | 8/2007 | Rolland et al. |
| 2007/0201736 A1 | 8/2007 | Klingensmith et al. |
| 2007/0206193 A1 | 9/2007 | Pesach |
| 2007/0208276 A1 | 9/2007 | Kornkven Volk et al. |
| 2007/0225220 A1 | 9/2007 | Ming et al. |
| 2007/0225590 A1 | 9/2007 | Ramos |
| 2007/0229801 A1 | 10/2007 | Tearney et al. |
| 2007/0232872 A1 | 10/2007 | Prough et al. |
| 2007/0232874 A1 | 10/2007 | Ince |
| 2007/0232890 A1 | 10/2007 | Hirota |
| 2007/0232891 A1 | 10/2007 | Hirota |
| 2007/0232892 A1 | 10/2007 | Hirota |
| 2007/0232893 A1 | 10/2007 | Tanioka |
| 2007/0232933 A1 | 10/2007 | Gille et al. |
| 2007/0238957 A1 | 10/2007 | Yared |
| 2007/0247033 A1 | 10/2007 | Eidenschink et al. |
| 2007/0250000 A1 | 10/2007 | Magnin et al. |
| 2007/0250036 A1 | 10/2007 | Volk et al. |
| 2007/0258094 A1 | 11/2007 | Izatt et al. |
| 2007/0260138 A1 | 11/2007 | Feldman et al. |
| 2007/0278389 A1 | 12/2007 | Ajgaonkar et al. |
| 2007/0287914 A1 | 12/2007 | Cohen |
| 2008/0002183 A1 | 1/2008 | Yatagai et al. |
| 2008/0013093 A1 | 1/2008 | Izatt et al. |
| 2008/0015438 A1 | 1/2008 | Mehi et al. |
| 2008/0021275 A1 | 1/2008 | Tearney et al. |
| 2008/0027481 A1 | 1/2008 | Gilson et al. |
| 2008/0043024 A1 | 2/2008 | Schiwietz et al. |
| 2008/0045842 A1 | 2/2008 | Furnish |
| 2008/0051660 A1 | 2/2008 | Kakadaris et al. |
| 2008/0063304 A1 | 3/2008 | Russak et al. |
| 2008/0085041 A1 | 4/2008 | Breeuwer |
| 2008/0095465 A1 | 4/2008 | Mullick et al. |
| 2008/0095714 A1 | 4/2008 | Castella et al. |
| 2008/0097194 A1 | 4/2008 | Milner |
| 2008/0101667 A1 | 5/2008 | Begelman et al. |
| 2008/0108867 A1 | 5/2008 | Zhou |
| 2008/0114254 A1 | 5/2008 | Matcovitch et al. |
| 2008/0119739 A1 | 5/2008 | Vardi et al. |
| 2008/0124495 A1 | 5/2008 | Horn et al. |
| 2008/0125772 A1 | 5/2008 | Stone et al. |
| 2008/0139897 A1 | 6/2008 | Ainsworth et al. |
| 2008/0143707 A1 | 6/2008 | Mitchell |
| 2008/0146941 A1 | 6/2008 | Dala-Krishna |
| 2008/0147111 A1 | 6/2008 | Johnson et al. |
| 2008/0154128 A1 | 6/2008 | Milner |
| 2008/0161696 A1 | 7/2008 | Schmitt et al. |
| 2008/0171944 A1 | 7/2008 | Brenneman et al. |
| 2008/0175465 A1 | 7/2008 | Jiang et al. |
| 2008/0177138 A1 | 7/2008 | Courtney et al. |
| 2008/0177139 A1* | 7/2008 | Courtney ............ A61B 5/0062 600/109 |
| 2008/0177183 A1 | 7/2008 | Courtney et al. |
| 2008/0180683 A1 | 7/2008 | Kemp |
| 2008/0181477 A1 | 7/2008 | Izatt et al. |
| 2008/0187201 A1 | 8/2008 | Liang et al. |
| 2008/0228086 A1 | 9/2008 | Ilegbusi et al. |
| 2008/0247622 A1 | 10/2008 | Aylward et al. |
| 2008/0247716 A1 | 10/2008 | Thomas et al. |
| 2008/0262470 A1 | 10/2008 | Lee et al. |
| 2008/0262489 A1 | 10/2008 | Steinke |
| 2008/0269599 A1 | 10/2008 | Csavoy et al. |
| 2008/0281205 A1 | 11/2008 | Naghavi et al. |
| 2008/0281248 A1 | 11/2008 | Angheloiu et al. |
| 2008/0285043 A1 | 11/2008 | Fercher et al. |
| 2008/0287795 A1 | 11/2008 | Klingensmith et al. |
| 2008/0291463 A1 | 11/2008 | Milner et al. |
| 2008/0292173 A1 | 11/2008 | Hsieh et al. |
| 2008/0294034 A1 | 11/2008 | Krueger et al. |
| 2008/0298655 A1 | 12/2008 | Edwards |
| 2008/0306766 A1 | 12/2008 | Ozeki et al. |
| 2009/0009801 A1 | 1/2009 | Tabuki |
| 2009/0018393 A1 | 1/2009 | Dick et al. |
| 2009/0034813 A1 | 2/2009 | Dikmen et al. |
| 2009/0043191 A1 | 2/2009 | Castella et al. |
| 2009/0046295 A1 | 2/2009 | Kemp et al. |
| 2009/0052614 A1 | 2/2009 | Hempel et al. |
| 2009/0069843 A1 | 3/2009 | Agnew |
| 2009/0079993 A1 | 3/2009 | Yatagai et al. |
| 2009/0088650 A1 | 4/2009 | Corl |
| 2009/0093980 A1 | 4/2009 | Kemp et al. |
| 2009/0122320 A1 | 5/2009 | Petersen et al. |
| 2009/0138544 A1 | 5/2009 | Wegenkittl et al. |
| 2009/0149739 A9 | 6/2009 | Maschke |
| 2009/0156941 A1 | 6/2009 | Moore |
| 2009/0174886 A1 | 7/2009 | Inoue |
| 2009/0174931 A1 | 7/2009 | Huber et al. |
| 2009/0177090 A1 | 7/2009 | Grunwald et al. |
| 2009/0177183 A1 | 7/2009 | Pinkernell et al. |
| 2009/0195514 A1 | 8/2009 | Glynn et al. |
| 2009/0196470 A1 | 8/2009 | Carl et al. |
| 2009/0198125 A1 | 8/2009 | Nakabayashi et al. |
| 2009/0203991 A1 | 8/2009 | Papaioannou et al. |
| 2009/0264768 A1 | 10/2009 | Courtney et al. |
| 2009/0269014 A1 | 10/2009 | Winberg et al. |
| 2009/0270695 A1 | 10/2009 | McEowen |
| 2009/0284322 A1 | 11/2009 | Harrison et al. |
| 2009/0284332 A1 | 11/2009 | Moore et al. |
| 2009/0284749 A1 | 11/2009 | Johnson et al. |
| 2009/0290167 A1 | 11/2009 | Flanders et al. |
| 2009/0292048 A1 | 11/2009 | Li et al. |
| 2009/0299195 A1 | 12/2009 | Muller et al. |
| 2009/0299284 A1 | 12/2009 | Holman et al. |
| 2009/0318951 A1 | 12/2009 | Kashkarov et al. |
| 2009/0326634 A1 | 12/2009 | Vardi |
| 2010/0007669 A1 | 1/2010 | Bethune et al. |
| 2010/0030042 A1 | 2/2010 | Denninghoff et al. |
| 2010/0061611 A1 | 3/2010 | Xu et al. |
| 2010/0063400 A1 | 3/2010 | Hall et al. |
| 2010/0087732 A1 | 4/2010 | Eberle et al. |
| 2010/0094125 A1 | 4/2010 | Younge et al. |
| 2010/0094127 A1 | 4/2010 | Xu |
| 2010/0094135 A1 | 4/2010 | Fang-Yen et al. |
| 2010/0094143 A1 | 4/2010 | Mahapatra et al. |
| 2010/0113919 A1 | 5/2010 | Maschke |
| 2010/0125238 A1 | 5/2010 | Lye et al. |
| 2010/0125268 A1 | 5/2010 | Gustus et al. |
| 2010/0125648 A1 | 5/2010 | Zaharia et al. |
| 2010/0128348 A1 | 5/2010 | Taverner |
| 2010/0152717 A1 | 6/2010 | Keeler |
| 2010/0160788 A1 | 6/2010 | Davies et al. |
| 2010/0161023 A1 | 6/2010 | Cohen et al. |
| 2010/0168714 A1 | 7/2010 | Burke et al. |
| 2010/0179421 A1 | 7/2010 | Tupin |
| 2010/0179426 A1 | 7/2010 | Davies et al. |
| 2010/0220334 A1 | 9/2010 | Condit et al. |
| 2010/0226607 A1 | 9/2010 | Zhang et al. |
| 2010/0234736 A1 | 9/2010 | Corl |
| 2010/0249601 A1 | 9/2010 | Courtney |
| 2010/0256616 A1 | 10/2010 | Katoh et al. |
| 2010/0272432 A1 | 10/2010 | Johnson |
| 2010/0284590 A1 | 11/2010 | Peng et al. |
| 2010/0290693 A1 | 11/2010 | Cohen et al. |
| 2010/0331950 A1 | 12/2010 | Strommer |
| 2011/0010925 A1 | 1/2011 | Nix et al. |
| 2011/0021919 A1 | 1/2011 | Mehi et al. |
| 2011/0021926 A1 | 1/2011 | Spencer et al. |
| 2011/0025853 A1 | 2/2011 | Richardson |
| 2011/0026797 A1 | 2/2011 | Declerck et al. |
| 2011/0032533 A1 | 2/2011 | Izatt et al. |
| 2011/0034801 A1 | 2/2011 | Baumgart |
| 2011/0044546 A1 | 2/2011 | Pan et al. |
| 2011/0066073 A1 | 3/2011 | Kuiper et al. |
| 2011/0071401 A1 | 3/2011 | Hastings et al. |
| 2011/0072405 A1 | 3/2011 | Chen et al. |
| 2011/0077528 A1 | 3/2011 | Kemp et al. |
| 2011/0080591 A1 | 4/2011 | Johnson et al. |

(56) References Cited

U.S. PATENT DOCUMENTS

| | | |
|---|---|---|
| 2011/0087104 A1 | 4/2011 | Moore et al. |
| 2011/0137140 A1 | 6/2011 | Tearney et al. |
| 2011/0144502 A1 | 6/2011 | Zhou et al. |
| 2011/0152771 A1 | 6/2011 | Milner et al. |
| 2011/0157597 A1 | 6/2011 | Lu et al. |
| 2011/0160586 A1 | 6/2011 | Li et al. |
| 2011/0178413 A1 | 7/2011 | Schmitt et al. |
| 2011/0190586 A1 | 8/2011 | Kemp |
| 2011/0216378 A1 | 9/2011 | Poon et al. |
| 2011/0220985 A1 | 9/2011 | Son et al. |
| 2011/0238061 A1 | 9/2011 | van der Weide et al. |
| 2011/0238083 A1 | 9/2011 | Moll et al. |
| 2011/0245669 A1 | 10/2011 | Zhang |
| 2011/0249094 A1 | 10/2011 | Wang et al. |
| 2011/0257545 A1 | 10/2011 | Suri |
| 2011/0264125 A1 | 10/2011 | Wilson et al. |
| 2011/0274329 A1 | 11/2011 | Mathew et al. |
| 2011/0282334 A1 | 11/2011 | Groenhoff |
| 2011/0301684 A1 | 12/2011 | Fischell et al. |
| 2011/0306995 A1 | 12/2011 | Moberg |
| 2011/0319752 A1 | 12/2011 | Steinberg |
| 2012/0004529 A1 | 1/2012 | Tolkowsky et al. |
| 2012/0004668 A1 | 1/2012 | Wallace et al. |
| 2012/0013914 A1 | 1/2012 | Kemp et al. |
| 2012/0016344 A1 | 1/2012 | Kusakabe |
| 2012/0016395 A1 | 1/2012 | Olson |
| 2012/0022360 A1 | 1/2012 | Kemp |
| 2012/0026503 A1 | 2/2012 | Lewandowski et al. |
| 2012/0029007 A1 | 2/2012 | Graham et al. |
| 2012/0059253 A1 | 3/2012 | Wang et al. |
| 2012/0059368 A1 | 3/2012 | Takaoka et al. |
| 2012/0062843 A1 | 3/2012 | Ferguson et al. |
| 2012/0065481 A1 | 3/2012 | Hunter et al. |
| 2012/0071823 A1 | 3/2012 | Chen |
| 2012/0071838 A1 | 3/2012 | Fojtik |
| 2012/0075638 A1 | 3/2012 | Rollins et al. |
| 2012/0083696 A1 | 4/2012 | Kitamura |
| 2012/0095340 A1 | 4/2012 | Smith |
| 2012/0095372 A1 | 4/2012 | Sverdlik et al. |
| 2012/0108943 A1 | 5/2012 | Bates et al. |
| 2012/0113108 A1 | 5/2012 | Dala-Krishna |
| 2012/0116353 A1 | 5/2012 | Arnold et al. |
| 2012/0130243 A1 | 5/2012 | Balocco et al. |
| 2012/0130247 A1 | 5/2012 | Waters et al. |
| 2012/0136259 A1 | 5/2012 | Milner et al. |
| 2012/0136427 A1 | 5/2012 | Palmaz et al. |
| 2012/0137075 A1 | 5/2012 | Vorbach |
| 2012/0155734 A1 | 6/2012 | Barratt et al. |
| 2012/0158101 A1 | 6/2012 | Stone et al. |
| 2012/0162660 A1 | 6/2012 | Kemp |
| 2012/0165661 A1 | 6/2012 | Kemp et al. |
| 2012/0170848 A1 | 7/2012 | Kemp et al. |
| 2012/0172698 A1 | 7/2012 | Teo et al. |
| 2012/0176607 A1 | 7/2012 | Ott |
| 2012/0184853 A1 | 7/2012 | Waters |
| 2012/0184859 A1 | 7/2012 | Shah et al. |
| 2012/0184977 A1 | 7/2012 | Wolf |
| 2012/0197113 A1 | 8/2012 | Courtney |
| 2012/0215094 A1 | 8/2012 | Rahimian et al. |
| 2012/0220836 A1 | 8/2012 | Alpert et al. |
| 2012/0220851 A1 | 8/2012 | Razansky et al. |
| 2012/0220865 A1 | 8/2012 | Brown et al. |
| 2012/0220874 A1 | 8/2012 | Hancock et al. |
| 2012/0220883 A1 | 8/2012 | Manstrom et al. |
| 2012/0224751 A1 | 9/2012 | Kemp et al. |
| 2012/0226153 A1 | 9/2012 | Brown et al. |
| 2012/0230565 A1 | 9/2012 | Steinberg et al. |
| 2012/0232400 A1 | 9/2012 | Dickinson et al. |
| 2012/0238869 A1 | 9/2012 | Schmitt et al. |
| 2012/0238956 A1 | 9/2012 | Yamada et al. |
| 2012/0244043 A1 | 9/2012 | Leblanc et al. |
| 2012/0250028 A1 | 10/2012 | Schmitt et al. |
| 2012/0253186 A1 | 10/2012 | Simpson et al. |
| 2012/0253192 A1 | 10/2012 | Cressman |
| 2012/0253276 A1 | 10/2012 | Govari et al. |
| 2012/0257210 A1 | 10/2012 | Whitney et al. |
| 2012/0262720 A1 | 10/2012 | Brown et al. |
| 2012/0265077 A1 | 10/2012 | Gille et al. |
| 2012/0265268 A1 | 10/2012 | Blum et al. |
| 2012/0265296 A1 | 10/2012 | McNamara et al. |
| 2012/0271170 A1 | 10/2012 | Emelianov et al. |
| 2012/0271175 A1 | 10/2012 | Moore et al. |
| 2012/0271339 A1 | 10/2012 | O'Beirne et al. |
| 2012/0274338 A1 | 11/2012 | Baks et al. |
| 2012/0276390 A1 | 11/2012 | Ji et al. |
| 2012/0277722 A1 | 11/2012 | Gerber et al. |
| 2012/0279764 A1 | 11/2012 | Jiang et al. |
| 2012/0283758 A1 | 11/2012 | Miller et al. |
| 2012/0289987 A1 | 11/2012 | Wilson et al. |
| 2012/0299439 A1 | 11/2012 | Huang |
| 2012/0310081 A1 | 12/2012 | Adler et al. |
| 2012/0310332 A1 | 12/2012 | Murray et al. |
| 2012/0319535 A1 | 12/2012 | Dausch |
| 2012/0323075 A1 | 12/2012 | Younge et al. |
| 2012/0323127 A1 | 12/2012 | Boyden et al. |
| 2012/0330141 A1 | 12/2012 | Brown et al. |
| 2013/0015975 A1 | 1/2013 | Huennekens et al. |
| 2013/0023762 A1 | 1/2013 | Huennekens et al. |
| 2013/0023763 A1 | 1/2013 | Huennekens et al. |
| 2013/0026655 A1 | 1/2013 | Lee et al. |
| 2013/0030295 A1 | 1/2013 | Huennekens et al. |
| 2013/0030303 A1 | 1/2013 | Ahmed et al. |
| 2013/0030410 A1 | 1/2013 | Drasler et al. |
| 2013/0053949 A1 | 2/2013 | Pintor et al. |
| 2013/0109958 A1 | 5/2013 | Baumgart et al. |
| 2013/0109959 A1 | 5/2013 | Baumgart et al. |
| 2013/0137980 A1 | 5/2013 | Waters et al. |
| 2013/0150716 A1 | 6/2013 | Stigall et al. |
| 2013/0158594 A1 | 6/2013 | Carrison et al. |
| 2013/0218201 A1 | 8/2013 | Obermiller et al. |
| 2013/0218267 A1 | 8/2013 | Braido et al. |
| 2013/0223789 A1 | 8/2013 | Lee et al. |
| 2013/0223798 A1 | 8/2013 | Jenner et al. |
| 2013/0296704 A1 | 11/2013 | Magnin et al. |
| 2013/0303907 A1* | 11/2013 | Corl .......... A61B 8/12 600/441 |
| 2013/0303920 A1 | 11/2013 | Corl |
| 2013/0310698 A1 | 11/2013 | Judell et al. |
| 2013/0331820 A1 | 12/2013 | Itou et al. |
| 2013/0338766 A1 | 12/2013 | Hastings et al. |
| 2013/0339958 A1 | 12/2013 | Droste et al. |
| 2013/0345556 A1 | 12/2013 | Courtney et al. |
| 2014/0039294 A1 | 2/2014 | Jiang |
| 2014/0073929 A1 | 3/2014 | Mehi et al. |
| 2014/0107490 A1 | 4/2014 | Fearnot et al. |
| 2014/0180067 A1 | 6/2014 | Stigall et al. |
| 2014/0180128 A1 | 6/2014 | Corl |
| 2014/0187963 A1* | 7/2014 | Corl .......... A61B 8/54 600/467 |
| 2014/0200438 A1 | 7/2014 | Millett et al. |

FOREIGN PATENT DOCUMENTS

| | | |
|---|---|---|
| EP | 2438877 A2 | 4/2012 |
| GB | 2280261 A | 1/1995 |
| JP | 02084946 A | 3/1990 |
| JP | 2000-262461 A | 9/2000 |
| JP | 2000-292260 A | 10/2000 |
| JP | 2001-125009 A | 5/2001 |
| JP | 2001-272331 A | 10/2001 |
| JP | 2002-374034 A | 12/2002 |
| JP | 2003-143783 A | 5/2003 |
| JP | 2003-172690 A | 6/2003 |
| JP | 2003-256876 A | 9/2003 |
| JP | 2003-287534 A | 10/2003 |
| JP | 2003290227 A | 10/2003 |
| JP | 2005-274380 A | 10/2005 |
| JP | 2006-184284 A | 7/2006 |
| JP | 2006-266797 A | 10/2006 |
| JP | 2006-313158 A | 11/2006 |
| JP | 2007-024677 A | 2/2007 |
| JP | 2009-233001 A | 10/2009 |
| JP | 2011-56786 A | 3/2011 |
| WO | 91/01156 A1 | 2/1991 |

(56) References Cited

FOREIGN PATENT DOCUMENTS

| | | |
|---|---|---|
| WO | 92/16865 A1 | 10/1992 |
| WO | 93/06213 A1 | 4/1993 |
| WO | 93/08829 A1 | 5/1993 |
| WO | 199407418 A1 | 4/1994 |
| WO | 98/38907 A1 | 9/1998 |
| WO | 98/57583 A1 | 12/1998 |
| WO | 00/11511 A1 | 3/2000 |
| WO | 00/044296 A1 | 8/2000 |
| WO | 01/11409 A2 | 2/2001 |
| WO | 03/062802 A2 | 7/2003 |
| WO | 03/073950 A1 | 9/2003 |
| WO | 2004/010856 A1 | 2/2004 |
| WO | 2004/023992 A1 | 3/2004 |
| WO | 2004/096049 A2 | 11/2004 |
| WO | 2005/047813 A1 | 5/2005 |
| WO | 2005/106695 A2 | 11/2005 |
| WO | 2006/029634 A2 | 3/2006 |
| WO | 2006/037132 A1 | 4/2006 |
| WO | 2006/039091 A2 | 4/2006 |
| WO | 2006/061829 A1 | 6/2006 |
| WO | 2006/068875 A2 | 6/2006 |
| WO | 2006/111704 A1 | 10/2006 |
| WO | 2006/119416 A2 | 11/2006 |
| WO | 2006/121851 A2 | 11/2006 |
| WO | 2006/130802 A2 | 12/2006 |
| WO | 2007/002685 A2 | 1/2007 |
| WO | 2007/025230 A2 | 3/2007 |
| WO | 2007/045690 A1 | 4/2007 |
| WO | 2007/058895 A2 | 5/2007 |
| WO | 2007/067323 A2 | 6/2007 |
| WO | 2007/084995 A2 | 7/2007 |
| WO | 2008/058084 A2 | 5/2008 |
| WO | 2008/069991 A1 | 6/2008 |
| WO | 2008/107905 A2 | 9/2008 |
| WO | 2009/009799 A1 | 1/2009 |
| WO | 2009/009801 A1 | 1/2009 |
| WO | 2009/046431 A1 | 4/2009 |
| WO | 2009/121067 A1 | 10/2009 |
| WO | 2009/137704 A1 | 11/2009 |
| WO | 2011/06886 A2 | 1/2011 |
| WO | 2011/038048 A1 | 3/2011 |
| WO | 2011/081688 A1 | 7/2011 |
| WO | 2012/003369 A2 | 1/2012 |
| WO | 2012/061935 A1 | 5/2012 |
| WO | 2012/071388 A2 | 5/2012 |
| WO | 2012/087818 A1 | 6/2012 |
| WO | 2012/098194 A1 | 7/2012 |
| WO | 2012/109676 A1 | 8/2012 |
| WO | 2012/130289 A1 | 10/2012 |
| WO | 2012/154767 A2 | 11/2012 |
| WO | 2012/155040 A1 | 11/2012 |
| WO | 2013/033414 A1 | 3/2013 |
| WO | 2013/033415 A2 | 3/2013 |
| WO | 2013/033418 A1 | 3/2013 |
| WO | 2013/033489 A1 | 3/2013 |
| WO | 2013/033490 A1 | 3/2013 |
| WO | 2013/033592 A1 | 3/2013 |
| WO | 2013/126390 A1 | 8/2013 |
| WO | 2013170143 A1 | 11/2013 |
| WO | 2014/109879 A1 | 7/2014 |

OTHER PUBLICATIONS

International Search Report and Written Opinion dated Apr. 14, 2014, for International Patent Application No. PCT/US2013/076148, filed Dec. 18, 2013 (8 pages).
International Search Report and Written Opinion dated Apr. 21, 2014, for International Patent Application No. PCT/US2013/076015, filed Dec. 18, 2013 (7 pages).
International Search Report and Written Opinion dated Apr. 23, 2014, for International Patent Application No. PCT/US2013/075328, filed Dec. 16, 2013 (8 pages).
International Search Report and Written Opinion dated Apr. 29, 2014, for International Patent Application No. PCT/US13/76093, filed Dec. 18, 2013 (6 pages).
International Search Report and Written Opinion dated Apr. 9, 2014, for International Patent Application No. PCT/US13/75089, filed Dec. 13, 2013 (7 pages).
International Search Report and Written Opinion dated Feb. 21, 2014, for International Patent Application No. PCT/US13/76053, filed Dec. 18, 2013 (9 pages).
International Search Report and Written Opinion dated Feb. 21, 2014, for International Patent Application No. PCT/US2013/076965, filed Dec. 20, 2013 (6 pages).
International Search Report and Written Opinion dated Feb. 27, 2014, for International Patent Application No. PCT/US13/75416, filed Dec. 16, 2013 (7 pages).
International Search Report and Written Opinion dated Feb. 28, 2014, for International Patent Application No. PCT/US13/75653, filed Dec. 17, 2013 (7 pages).
International Search Report and Written Opinion dated Feb. 28, 2014, for International Patent Application No. PCT/US13/75990, filed Dec. 18, 2013 (7 pages).
International Search Report and Written Opinion dated Jan. 16, 2009, for International Patent Application No. PCT/US08/78963 filed on Oct. 6, 2008 (7 Pages).
International Search Report and Written Opinion dated Jul. 30, 2014, for International Patent Application No. PCT/US14/21659, filed Mar. 7, 2014 (15 pages).
International Search Report and Written Opinion dated Mar. 10, 2014, for International Patent Application No. PCT/US2013/076212, filed Dec. 18, 2013 (8 pages).
International Search Report and Written Opinion dated Mar. 11, 2014, for International Patent Application No. PCT/US13/76173, filed Dec. 16, 2013 (9 pages).
International Search Report and Written Opinion dated Mar. 11, 2014, for International Patent Application No. PCT/US13/76449, filed Dec. 19, 2013 (9 pages).
International Search Report and Written Opinion dated Mar. 18, 2014, for International Patent Application No. PCT/US2013/076502, filed Dec. 19, 2013 (7 pages).
International Search Report and Written Opinion dated Mar. 18, 2014, for International Patent Application No. PCT/US2013/076788, filed Dec. 20, 2013 (7 pages).
International Search Report and Written Opinion dated Mar. 19, 2014, for International Patent Application No. PCT/US2013/076587, filed Dec. 19, 2013 (10 pages).
International Search Report and Written Opinion dated Mar. 19, 2014, for International Patent Application No. PCT/US2013/076909, filed Dec. 20, 2013 (7 pages).
International Search Report and Written Opinion dated Mar. 7, 2014, for International Patent Application No. PCT/US2013/076304, filed Dec. 18, 2013 (9 pages).
International Search Report and Written Opinion dated Mar. 7, 2014, for International Patent Application No. PCT/US2013/076480, filed Dec. 19, 2013 (8 pages).
International Search Report and Written Opinion dated Mar. 7, 2014, for International Patent Application No. PCT/US2013/076512, filed Dec. 19, 2013 (8 pages).
International Search Report and Written Opinion dated Mar. 7, 2014, for International Patent Application No. PCT/US2013/076531, filed Dec. 19, 2013 (10 pages).
Jakobovits et al., 1993, Analysis of homozygous mutant chimeric mice:deletion of the immunoglobulin heavy-chain joining region blocks B-cell development and antibody production, PNAS USA 90:2551-255.
Jakobovits et al., 1993, Germ-line transmission and expression of a human-derived yeast artificial chromosome, Nature 362:255-258.
Jang et al., 2002, Visualization of Coronary Atherosclerotic Plaques in Patients Using Optical Coherence Tomography: Comparison With Intravascular Ultrasound, Journal of the American College of Cardiology 39:604-609.
Jiang et al. 1992, Image registration of multimodality 3-D medical images by chamfer matching, Proc. SPIE 1660, Biomedical Image Processing and Three-Dimensional Microscopy, 356-366.

(56) References Cited

OTHER PUBLICATIONS

Johnson et al., 1993, Human antibody engineering: Current Opinion in Structural Biology, 3:564-571.

Jones et al., 1986, Replacing the complementarity-determining regions in a human antibody with those from a mouse, Nature, 321:522-525.

Juviler et al., 2008, Anorectal sepsis and fistula-in-ano, Surgical Technology International, 17:139-149.

Karapatis et al., 1998, Direct rapid tooling:a review of current research, Rapid Prototyping Journal, 4(2):77-89.

Karp et al., 2009, The benefit of time-of-flight in PET imaging, J Nucl Med 49:462-470.

Kelly et al., 2005, Detection of Vascular Adhesion Molecule-1 Expression Using a Novel Multimodal Nanoparticle, Circulation Research 96:327-336.

Kemp et al., 2005, Depth Resolved Optic Axis Orientation in Multiple Layered Anisotropic Tissues Measured with Enhanced Polarization Sensitive Optical Coherence Tomography, Optics Express 13(12):4507-4518.

Kersey et al., 1991, Polarization insensitive fiber optic Michelson interferometer, Electron. Lett. 27:518-520.

Kheir et al., 2012, Oxygen Gas-Filled Microparticles Provide Intravenous Oxygen Delivery, Science Translational Medicine 4(140):140ra88 (10 pages).

Khuri-Yakub et al., 2011, Capacitive micromachined ultrasonic transducers for medical imaging and therapy, J Micromech Microeng. 21(5):054004-054014.

Kirkman, 1991, Technique for flow reduction in dialysis access fistulas, Surg Gyn Obstet, 172(3):231-3.

Kohler et al., 1975, Continuous cultures of fused cells secreting antibody of predefined specificity, Nature, 256:495-7.

Koo et al., 2011, Diagnosis of IschemiaCausing Coronary Stenoses by Noninvasive Fractional Flow Reserve Computed From Coronary Computed Tomographic Angiograms, J Am Coll Cardiol 58(19):1989-1997.

Kozbor et al., 1984, A human hybrid myeloma for production of human monoclonal antibodies, J. Immunol., 133:3001-3005.

Kruth et al., 2003, Lasers and materials in selective laser sintering, Assembly Automation, 23(4):357-371.

Kumagai et al., 1994, Ablation of polymer films by a femtosecond high-peak-power Ti:sapphire laser at 798 nm, Applied Physics Letters, 65(14):1850-1852.

Larin et al., 2002, Noninvasive Blood Glucose Monitoring with Optical Coherence Tomography: a pilot study in human subjects, Diabetes Care, 25(12):2263-7.

Larin et al., 2004, Measurement of Refractive Index Variation of Physiological Analytes using Differential Phase OCT, Proc of SPIE 5325:31-34.

Laufer, 1996, Introduction to Optics and Lasers in Engineering, Cambridge University Press, Cambridge UK:156-162.

Lefevre et al., 2001, Stenting of bifurcation lesions:a rational approach, J. Interv. Cardiol., 14(6):573-585.

Li et al., 2000, Optical Coherence Tomography: Advanced Technology for the Endoscopic Imaging of Barrett's Esophagus, Endoscopy, 32(12):921-930.

Little et al., 1991, The underlying coronary lesion in myocardial infarction:implications for coronary angiography, Clinical Cardiology, 14(11):868-874.

Loo, 2004, Nanoshell Enabled Photonics-Based Imaging and Therapy of Cancer, Technology in Cancer Research & Treatment 3(1):33-40.

Machine translation of JP 2000-097846.

Machine translation of JP 2000-321034.

Machine translation of JP 2000-329534.

Machine translation of JP 2004-004080.

Maintz et al., 1998, An Overview of Medical Image Registration Methods, Technical Report UU-CS, (22 pages).

Mamas et al., 2010, Resting Pd/Pa measured with intracoronary pressure wire strongly predicts fractional flow reserve, Journal of Invasive Cardiology 22(6):260-265.

Marks et al., 1991, By-passing Immunization Human Antibodies from V-gene Libraries Displayed on Phage, J. Mol. Biol. 222:581-597.

Marks et al., 1992, By-Passing Immunization:Building High Affinity Human Antibodies by Chain Shuffling, BioTechnol., 10:779-783.

Maruno et al., 1991, Fluorine containing optical adhesives for optical communications systems, J. Appl. Polymer. Sci. 42:2141-2148.

McCafferty et al., 1990, Phage antibodies: filamentous phage displaying antibody variable domains, Nature 348:552-554.

Mendieta et al., 1996, Complementary sequence correlations with applications to reflectometry studies, Instrumentation and Development 3(6):37-46.

Mickley, 2008, Steal Syndrome-strategies to preserve vascular access and extremity, Nephrol Dial Transplant 23:19-24.

Miller et al., 2010, The MILLER banding procedure is an effective method for treating dialysis-associated steal syndrome, Kidney International 77:359-366.

Milstein et al., 1983, Hybrid hybridomas and their use in immunohistochemistry, Nature 305:537-540.

Mindlin et al., 1936, A force at a point of a semi-infinite solid, Physics, 7:195-202.

Morrison et al., 1984, Chimeric human antibody molecules: mouse antigen-binding domains with human constant region domains, PNAS 81:6851-6855.

Munson et al., 1980, Ligand: a versatile computerized approach for characterization of ligand-binding systems, Analytical Biochemistry, 107:220-239.

Nezam, 2008, High Speed Polygon-Scanner-Based Wavelength-Swept Laser Source in the Telescope-Less Configurations with Application in Optical Coherence Tomography, Optics Letters 33(15):1741-1743.

Nissen, 2001, Coronary Angiography and Intravascular Ultrasound, American Journal of Cardiology, 87 (suppl):15A-20A.

Nitenberg et al., 1995, Coronary vascular reserve in humans: a critical review of methods of evaluation and of interpretation of the results, Eur Heart J. 16(Suppl 1):7-21.

Notice of Reason(s) for Refusal dated Apr. 30, 2013, for Japanese Patent Application No. 2011-508677 for Optical Imaging Catheter for Aberation Balancing to Volcano Corporation, which application is a Japanese national stage entry of PCT/US2009/043181 with international filing date May 7, 2009, of the same title, published on Nov. 12, 2009, as WO 2009/137704, and accompanying English translation of the Notice of Reason(s) for Refusal and machine translations of JP11-56786 and JP2004-290548 (56 pages).

Nygren, 1982, Conjugation of horseradish peroxidase to Fab fragments with different homobifunctional and heterobifunctional cross-linking reagents. A comparative study, J. Histochem. and Cytochem. 30:407-412.

Oesterle et al., 1986, Angioplasty at coronary bifurcations: single-guide, two-wire technique, Cathet Cardiovasc Diagn., 12:57-63.

Okuno et al., 2003, Recent Advances in Optical Switches Using Silica-based PLC Technology, NTT Technical Review 1(7):20-30.

Oldenburg et al., 1998, Nanoengineering of Optical Resonances, Chemical Physics Letters 288:243-247.

Oldenburg et al., 2003, Fast-Fourier-Domain Delay Line for In Vivo Optical Coherence Tomography with a Polygonal Scanner, Applied Optics, 42(22):4606-4611.

Othonos, 1997, Fiber Bragg gratings, Review of Scientific Instruments 68(12):4309-4341.

Owens et al., 2007, A Survey of General-Purpose Computation on Graphics Hardware, Computer Graphics Forum 26(1):80-113.

Pain et al., 1981, Preparation of protein A—peroxidase mono conjugate using a heterobifunctional reagent, and its use in enzyme immunoassays, J Immunol Methods, 40:219-30.

Park et al., 2005, Real-time fiber-based multi-functional spectral-domain optical coherence tomography at 1.3 um., Optics Express 13(11):3931-3944.

Pasquesi et al., 2006, In vivo detection of exercise induced ultrastructural changes in genetically-altered murine skeletal muscle using polarization-sensitive optical coherence tomography, Optics Express 14(4):1547-1556.

(56) References Cited

OTHER PUBLICATIONS

Pepe et al., 2004, Limitations of the odds ratio in gauging the performance of a diagnostic, prognostic, or screening marker, American Journal of Epidemiology 159(9):882-890.
Persson et al., 1985, Acoustic impedance matching of medical ultrasound transducers, Ultrasonics, 23(2):83-89.
Placht et al., 2012, Fast time-of-flight camera based surface registration for radiotherapy patient positioning, Medical Physics 39(1):4-17.
Rabbani et al., 1999, Review: Strategies to achieve coronary arterial plaque stabilization, Cardiovascular Research 41:402-417.
Radvany et al., 2008, Plaque Excision in Management of Lower Extremity Peripheral Arterial Disease with the SilverHawk Atherectomy Catheter, Seminars in Interventional Radiology, 25(1):11-19.
Reddy et al., 1996, An FFT-Based Technique for Translation, Rotation, and Scale-Invariant Image Registration, IEEE Transaction on Image Processing 5(8):1266-1271.
Riechmann et al., 1988, Reshaping human antibodies for therapy, Nature, 332:323-327.
Rivers et al., 1992, Correction of steal syndrome secondary to hemodialysis access fistulas: a simplified quantitative technique, Surgery, 112(3):593-7.
Robbin et al., 2002, Hemodialysis Arteriovenous Fistula Maturity: US Evaluation, Radiology 225:59-64.
Rollins et al., 1998, In vivo video rate optical coherence tomography, Optics Express 3:219-229.
Sarunic et al., 2005, Instantaneous Complex Conjugate Resolved Spectral Domain and Swept-Source OCT Using 3×3 Fiber Couplers, Optics Express 13(3):957-967.
Satiani et al., 2009, Predicted Shortage of Vascular Surgeons in the United States, J. Vascular Surgery 50:946-952.
Schneider et al., 2006, T-banding: A technique for flow reduction of a hyper-functioning arteriovenous fistula, J Vasc Surg. 43(2):402-405.
Sen et al., 2012, Development and validation of a new adenosine-independent index of stenosis severity from coronary wave-intensity analysis, Journal of the American College of Cardiology 59(15):1392-1402.
Setta et al., 2005, Soft versus firm embryo transfer catheters for assisted reproduction: a systematic review and meta-analysis, Human Reproduction, 20(11):3114-3121.
Seward et al., 1996, Ultrasound Cardioscopy: Embarking on New Journey, Mayo Clinic Proceedings 71(7):629-635.
Shen et al., 2006, Eigengene-based linear discriminant model for tumor classification using gene expression microarray data, Bioinformatics 22(21):2635-2642.
Sihan et al., 2008, A novel approach to quantitative analysis of intraluminal optical coherence tomography imaging, Comput. Cardiol:1089-1092.
Abdi et al., 2010, Principal component analysis, Wiley Interdisciplinary Reviews: Computational Statistics 2:433-459.
Adler et al., 2007, Phase-Sensitive Optical Coherence Tomography at up to 370,000 Lines Per Second Using Buffered Fourier Domain Mode-Locked Lasers, Optics Letters, 32(6):626-628.
Agresti, 1996, Models for Matched Pairs, Chapter 8, An Introduction to Categorical Data Analysis, Wiley-Interscience A John Wiley & Sons, Inc., Publication, Hoboken, New Jersey.
Akasheh et al., 2004, Development of piezoelectric micromachined ultrasonic transducers, Sensors and Actuators A Physical, 111:275-287.
Amini et al., 1990, Using dynamic programming for solving variational problems in vision, IEEE Transactions on Pattern Analysis and Machine Intelligence, 12(9):855-867.
Bail et al., 1996, Optical coherence tomography with the "Spectral Radar"—Fast optical analysis in volume scatterers by short coherence interferometry, Optics Letters 21(14):1087-1089.
Bain, 2011, Privacy protection and face recognition, Chapter 3, Handbook of Face Recognition, Stan et al., Springer-Verlag.
Barnea et al., 1972, A class of algorithms for fast digital image registration, IEEE Trans. Computers, 21(2):179-186.

Blanchet et al., 1993, Laser Ablation and the Production of Polymer Films, Science, 262(5134):719-721.
Bonnema, 2008, Imaging Tissue Engineered Blood Vessel Mimics with Optical Tomography, College of Optical Sciences dissertation, University of Arizona (252 pages).
Bouma et al., 1999, Power-efficient nonreciprocal interferometer and linear-scanning fiber-optic catheter for optical coherence tomography, Optics Letters, 24(8):531-533.
Breiman, 2001, Random forests, Machine Learning 45:5-32.
Brown, 1992, A survey of image registration techniques, ACM Computing Surveys 24(4):325-376.
Bruining et al., 2009, Intravascular Ultrasound Registration/Integration with Coronary Angiography, Cardiology Clinics, 27(3):531-540.
Brummer, 1997, An euclidean distance measure between covariance matrices of speechcepstra for text-independent speaker recognition, in Proc. South African Symp. Communications and Signal Processing:167-172.
Burr et al., 2005, Searching for the Center of an Ellipse in Proceedings of the 17th Canadian Conference on Computational Geometry:260-263.
Canny, 1986, A computational approach to edge detection, IEEE Trans. Pattern Anal. Mach. Intell. 8:679-698.
Cavalli et al., 2010, Nanosponge formulations as oxygen delivery systems, International Journal of Pharmaceutics 402:254-257.
Choma et al., 2003, Sensitivity Advantage of Swept Source and Fourier Domain Optical Coherence Tomography, Optics Express 11(18):2183-2189.
Clarke et al., 1995, Hypoxia and myocardial ischaemia during peripheral angioplasty, Clinical Radiology, 50(5):301-303.
Collins, 1993, Coronary flow reserve, British Heart Journal 69:279-281.
Communication Mechanisms for Distributed Real-Time Applications, NI Developer Zone, http://zone.ni.eom/devzone/cda/tut/p/id/3105, accessed Jul. 23, 2007.
Cook, 2007, Use and misuse of receiver operating characteristic curve in risk prediction, Circulation 115(7):928-35.
D'Agostino et al., 2001, Validation of the Framingham coronary heart disease prediction score: results of a multiple ethnic group investigation, JAMA 286:180-187.
David et al., 1974, Protein iodination with solid-state lactoperoxidase, Biochemistry 13:1014-1021.
Davies et al., 1985, Plaque fissuring—the cause of acute myocardial infarction, sudden ischaemic death, and crescendo angina, British Heart Journal 53:363-373.
Davies et al., 1993, Risk of thrombosis in human atherosclerotic plaques: role of extracellular lipid, macrophage, and smooth muscle cell content, British Heart Journal 69:377-381.
Deterministic Data Streaming in Distributed Data Acquisition Systems, NI Developer Zone, "What is Developer Zone?", http://zone.ni.eom/devzone/cda/tut/p/id/3105, accessed Jul. 23, 2007.
Eigenwillig, 2008, K-Space Linear Fourier Domain Mode Locked Laser and Applications for Optical Coherence Tomography, Optics Express 16(12):8916-8937.
Elghanian et al., 1997, Selective colorimetric detection of polynucleotides based on the distance-dependent optical properties of gold nanoparticles, Science, 277(5329):1078-1080.
Ergun et al., 2003, Capacitive Micromachined Ultrasonic Transducers:Theory and Technology, Journal of Aerospace Engineering, 16(2):76-84.
Evans et al., 2006, Optical coherence tomography to identify intramucosa carcinoma and high-grade dysplasia in Barrett's esophagus, Clin Gast Hepat 4(1):38-43.
Fatemi et al., 1999, Vibro-acoustography: an imaging modality based on ultrasound-stimulated acoustic emission, PNAS U.S.A., 96(12):6603-6608.
Felzenszwalb et al., 2005, Pictorial Structures for Object Recognition, International Journal of Computer Vision, 61(1):55-79.
Ferring et al., 2008, Vasculature ultrasound for the pre-operative evaluation prior to arteriovenous fistula formation for haemodialysis: review of the evidence, Nephrol. Dial. Transplant. 23(6):1809-1815.
Fischler et al., 1973, The representation and matching of pictorial structures, IEEE Transactions on Computer 22:67-92.

(56) References Cited

OTHER PUBLICATIONS

Fleming et al., 2010, Real-time monitoring of cardiac radio-frequency ablation lesion formation using an optical coherence tomography forward-imaging catheter, Journal of Biomedical Optics 15 (3):030516-1 (3 pages).
Fookes et al., 2002, Rigid and non-rigid image registration and its association with mutual information:A review, Technical Report ISBN:1 86435 569 7, RCCVA, QUT.
Forstner & Moonen, 1999, A metric for covariance matrices, In Technical Report of the Dpt of Geodesy and Geoinformatics, Stuttgart University, 113-128.
Goel et al., 2006, Minimally Invasive Limited Ligation Endoluminal-assisted Revision (MILLER) for treatment of dialysis access-associated steal syndrome, Kidney Int 70(4):765-70.
Gotzinger et al., 2005, High speed spectral domain polarization sensitive optical coherence tomography of the human retina, Optics Express 13(25):10217-10229.
Gould et al., 1974, Physiologic basis for assessing critical coronary stenosis, American Journal of Cardiology, 33:87-94.
Griffiths et al., 1993, Human anti-self antibodies with high specificity from phage display libraries, The EMBO Journal, 12:725-734.
Griffiths et al., 1994, Isolation of high affinity human antibodies directly from large synthetic repertoires, The EMBO Journal, 13(14):3245-3260.
Grund et al., 2010, Analysis of biomarker data:logs, odds, ratios and ROC curves, Curr Opin HIV AIDS 5(6):473-479.
Harrison et al., 2011, Guidewire Stiffness: What's in a name?, J Endovasc Ther, 18(6):797-801.
Huber et al., 2005, Amplified, Frequency Swept Lasers for Frequency Domain Reflectometry and OCT Imaging: Design and Scaling Principles, Optics Express 13(9):3513-3528.
Huber et al., 2006, Fourier Domain Mode Locking (FDML): A New Laser Operating Regime and Applications for Optical Coherence Tomography, Optics Express 14(8):3225-3237.
International Search Report and Written Opinion dated Mar. 11, 2014, for International Patent Application No. PCT/US13/75675, filed Dec. 17, 2013 (7 pages).
International Search Report and Written Opinion dated Mar. 19, 2014, for International Patent Application No. PCT/US13/075353, filed Dec. 16, 2013 (8 pages).
International Search Report and Written Opinion dated Mar. 19, 2014, for International Application No. PCT/US13/75349 with International Filing Date Dec. 16, 2013 (10 pages).
Siwy et al., 2003, Electro-responsive asymmetric nanopores in polyimide with stable ion-current signal, Applied Physics A: Materials Science & Processing 76:781-785.
Smith et al., 1989, Absolute displacement measurements using modulation of the spectrum of white light in a Michelson interferometer, Applied Optics, 28(16):3339-3342.
Smith, 1997, The Scientist and Engineer's Guide to Digital Signal Processing, California Technical Publishing, San Diego, CA:432-436.
Soller, 2003, Polarization diverse optical frequency domain interferometry:All coupler implementation, Bragg Grating, Photosensitivity, and Poling in Glass Waveguides Conference MB4:30-32.
Song et al., 2012, Active tremor cancellation by a "Smart" handheld vitreoretinal microsurgical tool using swept source optical coherence tomography, Optics Express, 20(21):23414-23421.
Stenqvist et al., 1983, Stiffness of central venous catheters, Acta Anaesthesiol Scand., 2:153-157.
Strickland, 1970, Time-Domain Reflectometer Measurements, Tektronix, Beaverton, OR, (107 pages).
Strobl et al., 2009, An Introduction to Recursive Partitioning:Rationale, Application and Characteristics of Classification and Regression Trees, Bagging and Random Forests, Psychol Methods., 14(4):323-348.
Sutcliffe et al., 1986, Dynamics of UV laser ablation of organic polymer surfaces, Journal of Applied Physics, 60(9):3315-3322.
Suzuki, 2013, A novel guidewire approach for handling acute-angle bifurcations, J Inv Cardiol 25(1):48-54.
Tanimoto et al., 2008, A novel approach for quantitative analysis of intracoronary optical coherence tomography: high inter-observer agreement with computer-assisted contour detection, Cathet Cardiovascular Intervent., 72(2):228-235.
Tearney et al., 1997, In vivo Endoscopic Optical Biopsy with Optical Coherence Tomography, Science, 276:2037-2039.
Tonino et al., 2009, Fractional flow reserve versus angiography for guiding percutaneous coronary intervention, The New England Journal of Medicine, 360:213-224.
Toregeani et al., 2008, Evaluation of hemodialysis arteriovenous fistula maturation by color-flow Doppler ultrasound, J Vasc. Bras. 7(3):203-213.
Translation of Notice of Reason(s) for Refusal dated Apr. 30, 2014, for Japanese Patent Application No. 2011-508677, (5 pages).
Translation of Notice of Reason(s) for Refusal dated May 25, 2012, for Japanese Patent Application No. 2009-536425, (3 pages).
Translation of Notice of Reason(s) for Refusal dated Nov. 22, 2012, for Japanese Patent Application No. 2010-516304, (6 pages).
Traunecker et al., 1991, Bispecific single chain molecules (Janusins) target cytotoxic lymphocytes on HIV infected cells, EMBO J., 10:3655-3659.
Trolier-McKinstry et. al., 2004, Thin Film Piezoelectric for MEMS, Journal of Electroceramics 12:7-17.
Tuniz et al., 2010, Weaving the invisible thread: design of an optically invisible metamaterial fibre, Optics Express 18(17):18095-18105.
Turk et al., 1991, Eigenfaces for Recognition, Journal of Cognitive Neuroscience 3(1):71-86.
Tuzel et al., 2006, Region Covariance: A Fast Descriptor for Detection and Classification, European Conference on Computer Vision (ECCV).
Urban et al., 2010, Design of a Pressure Sensor Based on Optical Bragg Grating Lateral Deformation, Sensors (Basel), 10(12):11212-11225.
Vakhtin et al., 2003, Common-path interferometer for frequency-domain optical coherence tomography, Applied Optics, 42(34):6953-6958.
Vakoc et al., 2005, Phase-Resolved Optical Frequency Domain Imaging, Optics Express 13(14):5483-5493.
Verhoeyen et al., 1988, Reshaping human antibodies: grafting an antilysozyme activity, Science, 239:1534-1536.
Villard et al., 2002, Use of a blood substitute to determine instantaneous murine right ventricular thickening with optical coherence tomography, Circulation, 105:1843-1849.
Wang et al., 2002, Optimizing the Beam Patten of a Forward-Viewing Ring-Annular Ultrasound Array for Intravascular Imaging, Transactions on Ultrasonics, Ferroelectrics, and Frequency Control, 49(12).
Wang et al., 2006, Multiple biomarkers for the prediction of first major cardiovascular events and death, The New England Journal of Medicine, 355(25):2631-2639.
Wang et al., 2009, Robust Guidewire Tracking in Fluoroscopy, IEEE Conference on Computer Vision and Pattern Recognition—CVPR 2009:691-698.
Wang et al., 2011, In vivo intracardiac optical coherence tomography imaging through percutaneous access: toward image-guided radio-frequency ablation, J. Biomed. Opt. 0001 16(11):110505-1 (3 pages).
Waterhouse et. al., 1993, Combinatorial infection and in vivo recombination: a strategy for making large phage antibody repertoires, Nucleic Acids Res., 21:2265-2266.
Wegener, 2011, 3D Photonic Metamaterials and Invisibility Cloaks: The Method of Making, MEMS 2011, Cancun, Mexico, Jan. 23-27, 2011.
West et al., 1991, Arterial insufficiency in hemodialysis access procedures: correction by banding technique, Transpl Proc 23(2):1838-40.
Wyawahare et al., 2009, Image registration techniques: an overview, International Journal of Signal Processing, Image Processing and Pattern Recognition, 2(3):11-28.

(56) References Cited

OTHER PUBLICATIONS

Yaqoob et al., 2006, Methods and application areas of endoscopic optical coherence tomography, J. Biomed. Opt., 11, 063001-1-063001-19.

Yasuno et al., 2004, Polarization-sensitive complex Fourier domain optical coherence tomography for Jones matrix imaging of biological samples, Applied Physics Letters 85(15):3023-3025.

Zhang et al., 2004, Full range polarization-sensitive Fourier domain optical coherence tomography, Optics Express, 12(24):6033-6039.

Zitova et al., 2003, Image registration methods: A survey. Image and Vision Computing, 21(11):977-1000.

Van Der Heiden, Maurits S. et al "A High Resolution Ultrasonic Imaging System for the Detection of Cervical Cancer", 1996 IEEE Ultrasonics Symposium.

\* cited by examiner

ULTRASOUND IMAGING WITH VARIABLE LINE DENSITY

CROSS-REFERENCE TO RELATED APPLICATION

This application claims the benefit of, and priority to, U.S. Provisional Application Ser. No. 61/745,025, filed Dec. 21, 2012, the contents of which are incorporated by reference.

FIELD OF THE INVENTION

The invention generally relates to intravascular ultrasound imaging and to systems and methods to improve line density and image quality.

BACKGROUND

A vulnerable plaque is a kind of plaque on an artery wall characterized by a core layer of dead tissue covered with a very thin fibrous cap. This fibrous cap is prone to rupture, releasing bits of the dead tissue into the bloodstream. This material can then flow to the brain or heart and cause a stroke or a heart attack. Vulnerable plaques are identified in autopsies but existing medical imaging systems do not all provide good enough resolution to faithfully identify the thin structures involved.

Intravascular ultrasound (IVUS) is used to study arterial plaques. Typical IVUS systems use a long, thin catheter with an ultrasonic transducer at the tip. The catheter is inserted into a patient's arteries and rotated to capture a series of lines of image data. One rotational set of those lines can be composed into a 2D display giving a cross-sectional view of the artery. However, since the catheter rotates in an organic environment, subject to non-uniform stresses, the rotational speed is variable. As a result, if the system fires a series of scan lines at regular time intervals, there will not be any intrinsic grouping of scan lines into rotational sets. Instead, systems include a mechanical device that fires each scan line at a specific rotational position.

One such device is a rotary encoder. The hardware inside of a rotary encoder creates on distinct electrical signal per step of rotation. Because the hardware provides steps in powers of two, existing rotary encoders provide, for example, 512 or 1024 steps per revolution. IVUS systems are wired so that each step provides the electrical impulse that fires the transducer. To increase scan line density requires redesigning a system or making a new system to operate with a higher density rotary encoder. However, the problem is compounded by the recognition that rotary encoders can only have so many steps. Too many, and the electronics will not be able to faithfully detect each step speeds typical of IVUS systems.

SUMMARY

The invention provides an intravascular imaging system that uses a mechanical device to provide a set of trigger signals for each revolution of an imaging catheter and that capture patterns of scan lines for each set of trigger signals.

The system can be operated to capture two scan lines of data for each trigger signal thereby doubling scan line density compared to existing systems. Increased scan line density allows for operations that provide high quality, high-resolution images. For example, a high density of adjacent scanlines can be averaged, which greatly improves the signal-to-noise ratio, and thus the final resolution, of the image. Adjacent scan lines can be captured at different frequencies, which can aid in discriminating among blood and different tissue types. Different frequencies allows for the use of a fundamental frequency and one or more of its harmonics, i.e., harmonic imaging, which can improve resolution, reduce spurious artifacts, and improve SNR. Since an imaging system can capture very high resolution images of the tissue surrounding the catheter, the system can be used to view very delicate structures within a patient's arteries. Thus, systems and methods of the invention have the potential to be used in medical diagnostics for identifying very fine structures and possibly diagnosing such conditions as vulnerable plaque before those conditions become symptomatic.

In certain aspects, the invention provides a method for intravascular imaging that includes introducing an ultrasonic transducer into a vessel, the transducer being disposed at a distal portion of a catheter and using a module operably coupled to a proximal portion of the catheter to rotate the transducer and to provide a plurality of trigger signals. Each trigger signal triggers a first sequencer operation and a second sequencer operation.

The module may include a clock device, such as a rotary encoder, in which hardware is configured to define a maximum number of trigger signals that the module can provide per rotation of the catheter. The method provides for performing a number of sequencer operations per rotation greater than the maximum number of trigger signals provided by the clock device. Each sequencer operation can include stimulating the transducer to transmit an ultrasonic signal into the vessel, using the transducer to receive a backscattered signal from the vessel, or both. In some embodiments, the first sequencer operation involves ultrasonic imaging at a first frequency and the second sequencer operation involves imaging at a second frequency. In certain embodiments, the first sequencer operation involves only sending an ultrasonic signal and the second sequencer operation involves sending and receiving, e.g., to detect harmonics or interference from the sent signals. The first sequencer operation may be used to acquire a scanline with a short pulse and the second sequencer operation to acquire a scanline with a long pulse. Where the clock device includes hardware defining a maximum number of trigger signals that can be provided per full rotation of the catheter, methods include capturing a number of A lines of data per rotation of the catheter greater than the maximum number of trigger signals.

In related aspects, the invention provides a system for intravascular imaging. The system includes an ultrasonic catheter, a control system connected to the catheter, a rotary encoder operable to produce a plurality of rotary encodes per each 360° rotation of the catheter, and a processor in communication with the rotary encoder configured to issue varying patterns of transmit triggers in response to each plurality of rotary encodes.

In other aspects, the invention provides a system for intravascular imaging that uses an ultrasonic transducer disposed at a distal portion of a catheter and a module operably coupled to a proximal portion of the catheter. The system rotates the transducer and to provides a plurality of trigger signals. In response to each trigger signal, a processor triggers a plurality of sequencer operations. Preferably, the module includes a clock device such as a rotary encoder with hardware that defines a maximum number of trigger signals that the module can provide per rotation. The system can perform a number of sequencer operations per rotation greater than the maximum number of trigger signals provided by the rotary encoder.

In other aspects, the invention provides a method for intravascular imaging that proceeds by introducing an ultrasonic transducer into a vessel, the transducer being disposed at a distal portion of a catheter and using a module operably coupled to a proximal portion of the catheter to rotate the transducer 360° and to produce a plurality of trigger signals. For each trigger signal, a plurality of A lines of data are captured.

DETAILED DESCRIPTION

The invention provides systems and methods by which intravascular imaging can be performed with high line density, varying frequencies of scan lines, and patterns of scan lines other than one scan line per rotary encode.

Figure 1:
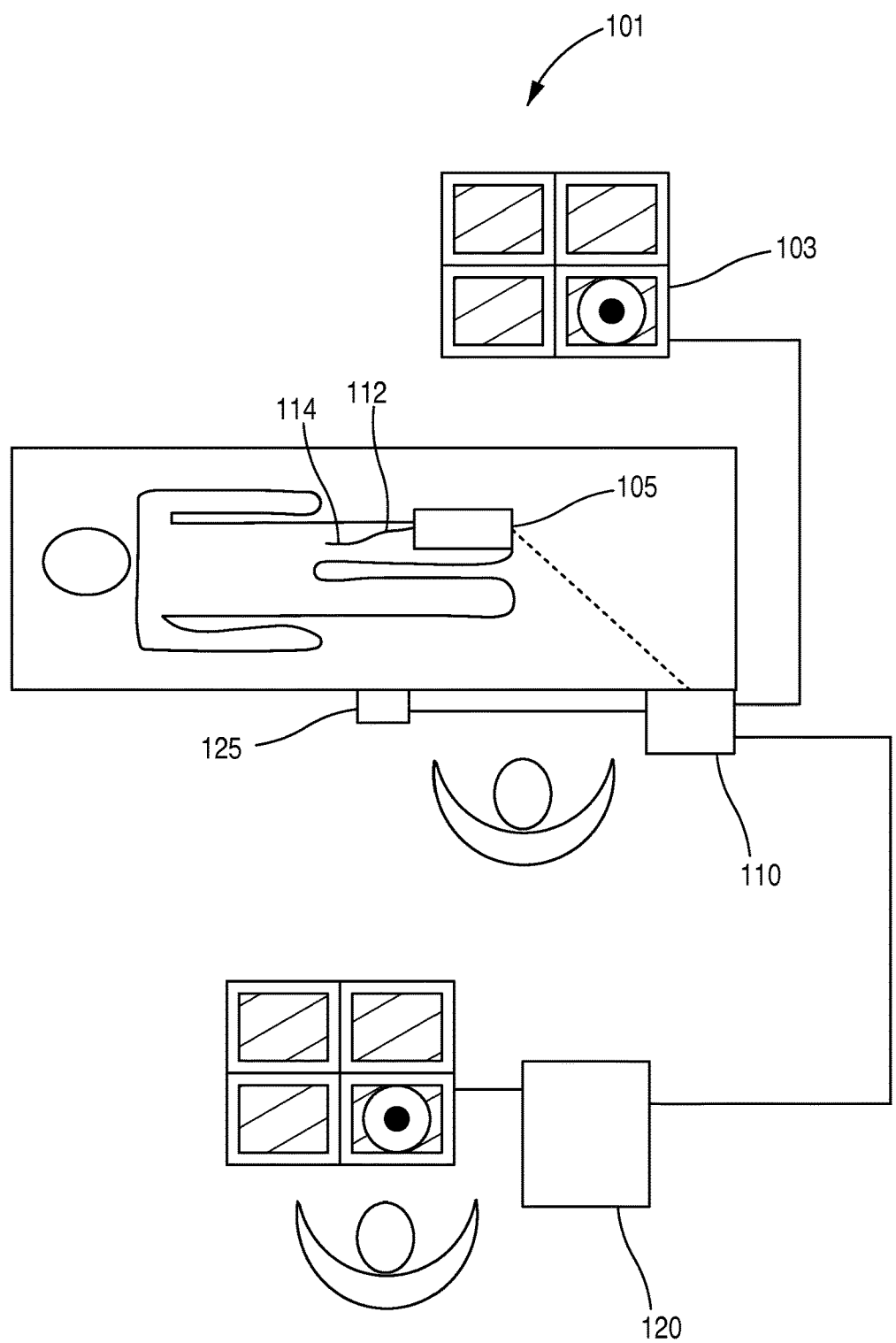
FIG. 1 shows a diagram of an exemplary IVUS system.

FIG. 1 shows a diagram of an exemplary IVUS system 101 according to certain embodiments of the invention. An operator uses control station 110 and optional navigational device 125 to operate catheter 112 via patient interface module (PIM) 105. At a distal tip of catheter 112 is an ultrasonic transducer 114. Computer device 120 works with PIM 105 to coordinate imaging operations. Imaging operations proceed by rotating an imaging mechanism via catheter 112 while transmitting a series of electrical impulses to transducer 114 which results in sonic impulses being sent into the patient's tissue. Backscatter from the ultrasonic impulses is received by transducer 114 and interpreted to provide an image on monitor 103. System 101 is operable for use during diagnostic ultrasound imaging of the peripheral and coronary vasculature of the patient. System 101 can be configured to automatically visualize boundary features, perform spectral analysis of vascular features, provide qualitative or quantitate blood flow data, or a combination thereof. Systems for IVUS suitable for use with the invention are discussed in U.S. Pat. No. 6,673,015; U.S. Pub. 2012/0265077; and U.S. Pat. No. RE40,608 E, the contents of which are incorporated by reference in their entirety for all purposes. Systems for IVUS are discussed in U.S. Pat. No. 5,771,895; U.S. Pub. 2009/0284332; U.S. Pub. 2009/0195514 A1; U.S. Pub. 2007/0232933; and U.S. Pub. 2005/0249391, the contents of each of which are hereby incorporated by reference in their entirety. It will appreciated that methods of the invention are operable with phased array IVUS, which can be performed using an imaging catheter with a lumen therethrough. The trigger signals described herein can be applied to individual ones of the ultrasonic transducers in a phased-array IVUS array. Phased array IVUS is described in U.S. Pub. 2013/0150716 to Stigall, the contents of which are incorporated by reference. A rotary encoder (discussed in more detail herein) can be used to drive a signal around an array in series, even where the phased array itself does not rotate.

Operation of system 101 employs a sterile, single use intravascular ultrasound imaging catheter 112. Catheter 112 is inserted into the coronary arteries and vessels of the peripheral vasculature under angiographic guidance. Catheters are described in U.S. Pat. No. 7,846,101; U.S. Pat. No. 5,771,895; U.S. Pat. No. 5,651,366; U.S. Pat. No. 5,176,141; U.S. Pub. 2012/0271170; U.S. Pub. 2012/0232400; U.S. Pub. 2012/0095340; U.S. Pub. 2009/0043191; U.S. Pub. 2004/0015065, the contents of which are incorporated by reference herein in their entirety for all purposes. System 101 may be integrated into existing and newly installed catheter laboratories (i.e., "cath labs" or "angiography suites"). The system configuration is flexible in order to fit into the existing catheter laboratory work flow and environment. For example, the system can include industry standard input/output interfaces for hardware such as navigation device 125, which can be a bedside mounted joystick. System 101 can include interfaces for one or more of an EKG system, exam room monitor, bedside rail mounted monitor, ceiling mounted exam room monitor, and server room computer hardware.

System 101 connects to the IVUS catheter 112 via PIM 105, which may contain a type CF (intended for direct cardiac application) defibrillator proof isolation boundary. All other input/output interfaces within the patient environment may utilize both primary and secondary protective earth connections to limit enclosure leakage currents. The primary protective earth connection for controller 125 and control station 110 can be provided through the bedside rail mount. A secondary connection may be via a safety ground wire directly to the bedside protective earth system. Monitor 103 and an EKG interface can utilize the existing protective earth connections of the monitor and EKG system and a secondary protective earth connection from the bedside protective earth bus to the main chassis potential equalization post. Monitor 103 may be, for example, a standard SXGA (1280×1024) exam room monitor. System 101 includes control system 120 to coordinate operations.

Computer device 120 generally includes one or more processor coupled to a memory. Any suitable processor can be included such as, for example, a general-purpose microprocessor, an application-specific integrated circuit, a massively parallel processing array, a field-programmable gate array, others, or a combination thereof. In some embodiments, computer 120 can include a high performance dual Xeon based system using an operating system such as Windows XP professional. Computer 120 may be provided as a single device (e.g., a desktop, laptop, or rack-mounted unit, or computer 120 may include different machines coupled together (e.g., a Beowulf cluster, a network of servers, a server operating with a local client terminal, other arrangements, or a combination thereof). A computer according to the invention generally includes a processor coupled to memory and one or more input/output (I/O) devices. A processor generally refers to a computer microchip such as the processor sold under the trademark CORE 17 by Intel (Santa Clara, Calif.).

Memory generally includes one or more devices for random access, storage, or both. Preferably, memory includes a tangible, non-transitory computer readable medium, and may be provided by one or more of a solid state drive (SSD), a magnetic disc drive (aka, "a hard drive"), flash memory, an optical drive, others, or a combination thereof.

An I/O device may include one or more of a monitor, keyboard, mouse, touchscreen, Wi-Fi card, cell antenna, Ethernet port, USB port, light, accelerometer, speaker, microphone, drive for removable disc, others, or a combination thereof. Preferably, any combination of computer in system 501 may communicate through the use of a network, which may include communication devices for internet communication, telephonic communication, others, or a combination thereof.

Computer device 120 may be configured to perform processing on more than one image modality (e.g., in parallel). For example, computer 120 may operate with real time intravascular ultrasound imaging while simultaneously running a tissue classification algorithm referred to as virtual histology (VH). The application software can include a DICOM3 compliant interface, a work list client interface, interfaces for connection to angiographic systems, or a combination thereof. Computer device 120 may be located in a separate control room, the exam room, or in an equipment room and may be coupled to one or more of a custom control station, a second control station, a joystick controller, a PS2 keyboard with touchpad, a mouse, or any other computer control device.

Computer device 120 may generally include one or more USB or similar interfaces for connecting peripheral equipment. Available USB devices for connection include the custom control stations, optional joystick 125, and a color printer. In some embodiments, computer 120 includes one or more of a USB 2.0 high speed interface, a 10/100/1000 baseT Ethernet network interface, AC power input, PS2 jack, potential equalization post, 1 GigE Ethernet interface, microphone & line inputs, line output VGA Video, DVI video interface, PIM interface, ECG interface, other connections, or a combination thereof. As shown in FIG. 1, computer device 120 is generally linked to control station 110.

Figure 2:
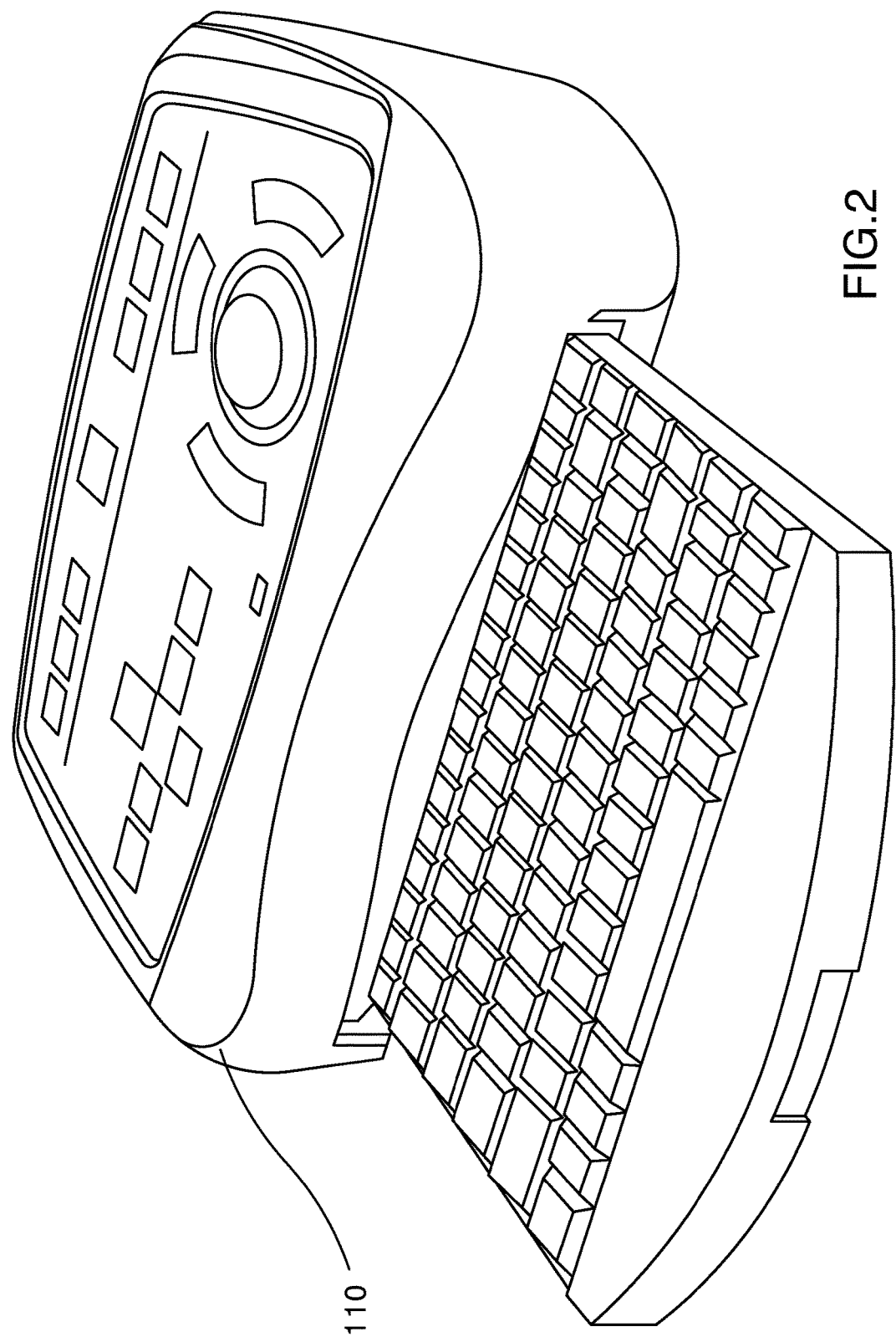
FIG. 2 depicts a control unit.

FIG. 2 shows a control station 110 according to certain embodiments. Control station 110 may be provided by any suitable device, such as a computer terminal (e.g., on a kiosk). In some embodiments, control station 110 is a purpose built device with a custom form factor. A slide out keyboard is located on the bottom for manual text entry. Control station 110 may be designed for different installations options. The station can be placed directly on a desktop surface. With the optional bedside mounting kit, control station 110 can be affixed directly to the bedside rail. This mounting kit is slipped over the rail and fixed in place by tightening two hand screws. Control station 110 can include a standard four hole VESA mount on the underside to allow other mounting configurations. Control station 110 may provide a simple-to-use interface with frequently-operated functions mapped to unique switches. Control station 110 may be powered from, and may communicate with, computer 120 using a standard USB 1.1 interface. The system may include a control panel 115. In some embodiments, multiple control panels 115 are mounted in both the exam room and/or the control room. A control station for use with the invention is discussed in U.S. Pat. No. 8,289,284, the contents of which are incorporated by reference in their entirety for all purposes.

Figure 3:
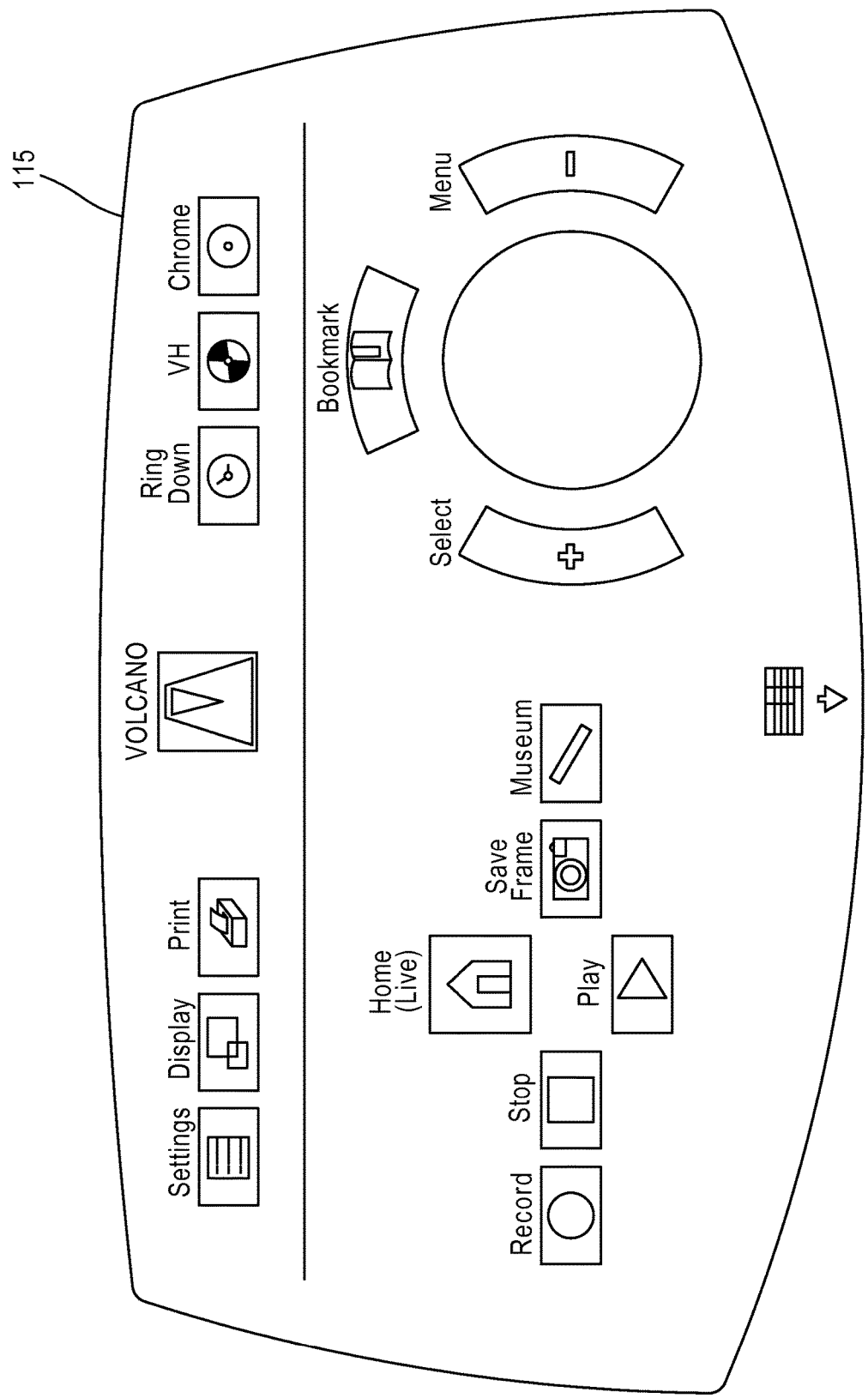
FIG. 3 illustrates the keypad of a control unit.

FIG. 3 shows an control panel 115 of control station 110 according to certain embodiments. Frequently-operated functions are mapped to contact closure switches. Those dome switches are covered with a membrane overlay. The use of dome switches provides a tactile feedback to the operator upon closure. Control panel 115 may include a pointing device such as a trackball to navigate a pointer on the graphical user interface of the system.

Control panel 115 may include several screen selection keys. The settings key is used to change system settings like date and time and also permits setting and editing default configurations. The display key may be used to provide enlarged view for printing. In some embodiments, the print key prints a 6×4 inch photo of the current image on the screen. Control panel 115 may include a ringdown key that toggles the operation of ringdown subtraction. A chroma key can turn blood flow operations on and off. The VH key can operate the virtual histology engine. A record, stop, play, and save frame key are included for video operation. Typically, the home key will operate to display the live image. A menu key provides access to measurement options such as diameter, length, and borders. Bookmark can be used while recording a loop to select specific areas of interest. Select (+) and Menu (−) keys are used to make selections.

In some embodiments, the system includes a joystick for navigational device 125. The joystick may be a sealed off-the-shelf USB pointing device used to move the cursor on the graphical user interface from the bedside. System 101 may include a control room monitor, e.g., an off-the-shelf 19" flat panel monitor with a native pixel resolution of 1280×1024 to accept DVI-D, DVI-I and VGA video inputs.

Control station 110 is operably coupled to PIM 115, from which catheter 112 extends. Catheter 112 includes an ultrasound transducer 114 located at the tip. Any suitable IVUS transducer may be used. For example, in some embodiments, transducer 114 is driven as a synthetic aperture imaging element. Imaging transducer 114 may be approximately 1 mm in diameter and 2.5 mm in length. In certain embodiments, transducer 114 includes a piezoelectric component such as, for example, lead zirconium nitrate or PZT ceramic. The transducer may be provided as an array of elements (e.g., 64), for example, bonded to a Kapton flexible circuit board providing one or more integrated circuits. This printed circuit assembly may rolled around a central metal tube, back filled with an acoustic backing material and bonded to the tip of catheter 114. In some embodiments, signals are passed to the system via a plurality of wires (e.g., 7) that run the full length of catheter 112. The wires are bonded to the transducer flex circuit at one end and to a mating connector in PIM 105 at the other. The PIM connector may also contains a configuration EPROM. The EPROM may contain the catheter's model and serial numbers and the calibration coefficients which are used by the system. The PIM 105 provides the patient electrical isolation, the beam steering, and the RF amplification. PIM 105 may additionally include a local microcontroller to monitor the performance of the system and reset the PIM to a known safe state in the event of loss of communication or system failure. PIM 105 may communicate with computer device 120 via a low speed RS232 serial link.

Figure 4:
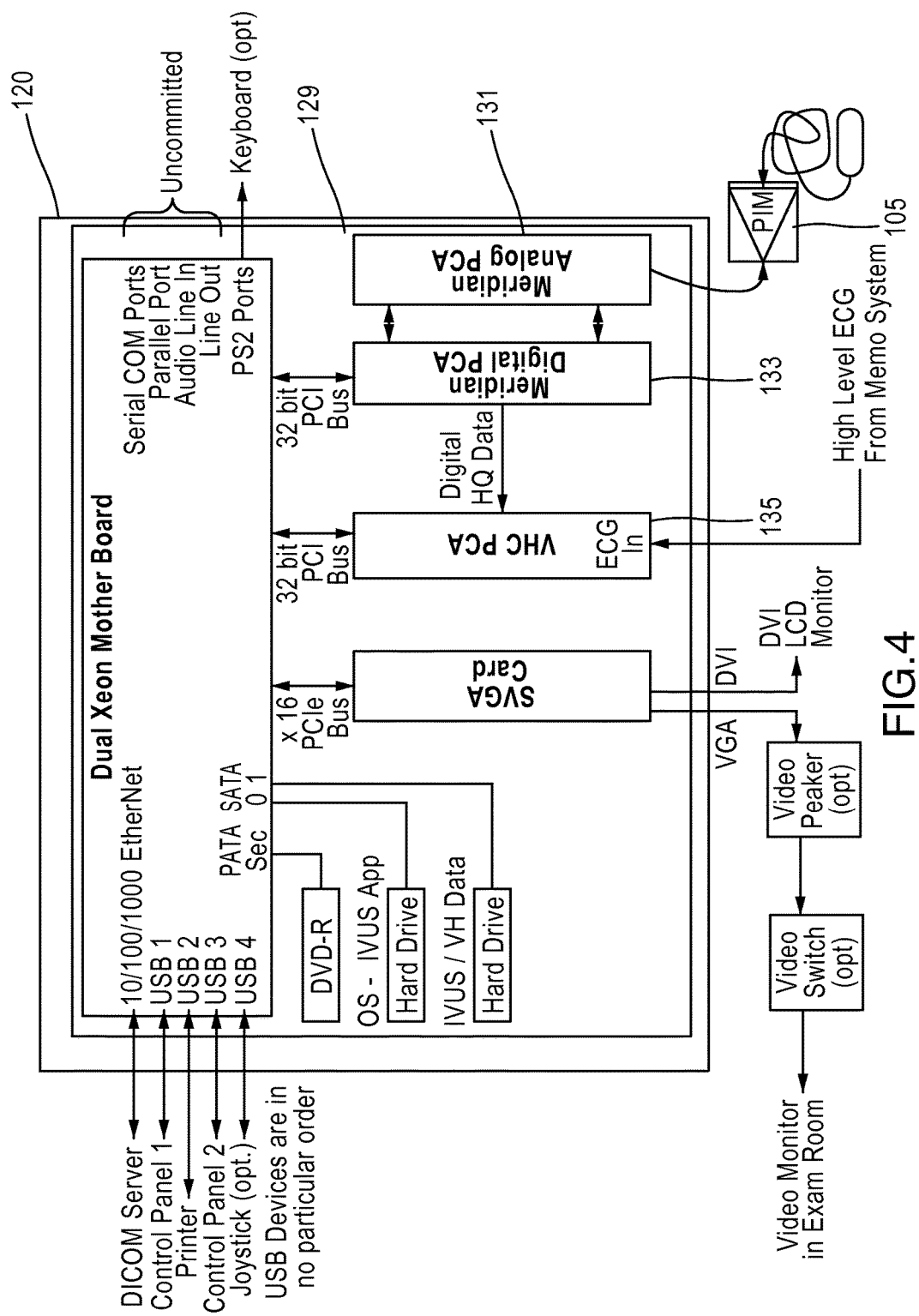
FIG. 4 presents a schematic diagram of a computer component of an IVUS system.

FIG. 4 describes components of computer device 120 according to certain embodiments. Computer device 120 may include a motherboard 129 that includes an IVUS signal generation and processing system. The signal generation and processing system may comprises an analog printed circuit assembly (PCA) 131, an digital PCA 133, one or more filter modules, and a VH board 135. Analog PCA 131 and digital PCA 133 are used to excite transducer 114 via catheter 112 and to receive and process the gray scale IVUS signals. The VH board 135 is used to capture and pre-process the IVUS RF signals and transfer them to the main VH processing algorithm as run by a computer processor system (e.g., dual Xeon processors). PIM 105 is directly connected to the analog PCA 131. A computer system that includes a computer, such as one like that depicted in FIG. 4, can be configured to perform the signal processing of the invention. Exemplary signal processing and systems therefore are discussed in U.S. Pat. No. 8,298,147; U.S. Pat. No. 8,187,191; U.S. Pat. No. 6,450,964; U.S. Pat. No. 5,485,845; U.S. Pub. 2012/0220874; U.S. Pub. 2012/0184853; and U.S. Pub. 2007/0232933, the contents of which are incorporated by reference herein in their entirety.

Figure 5:
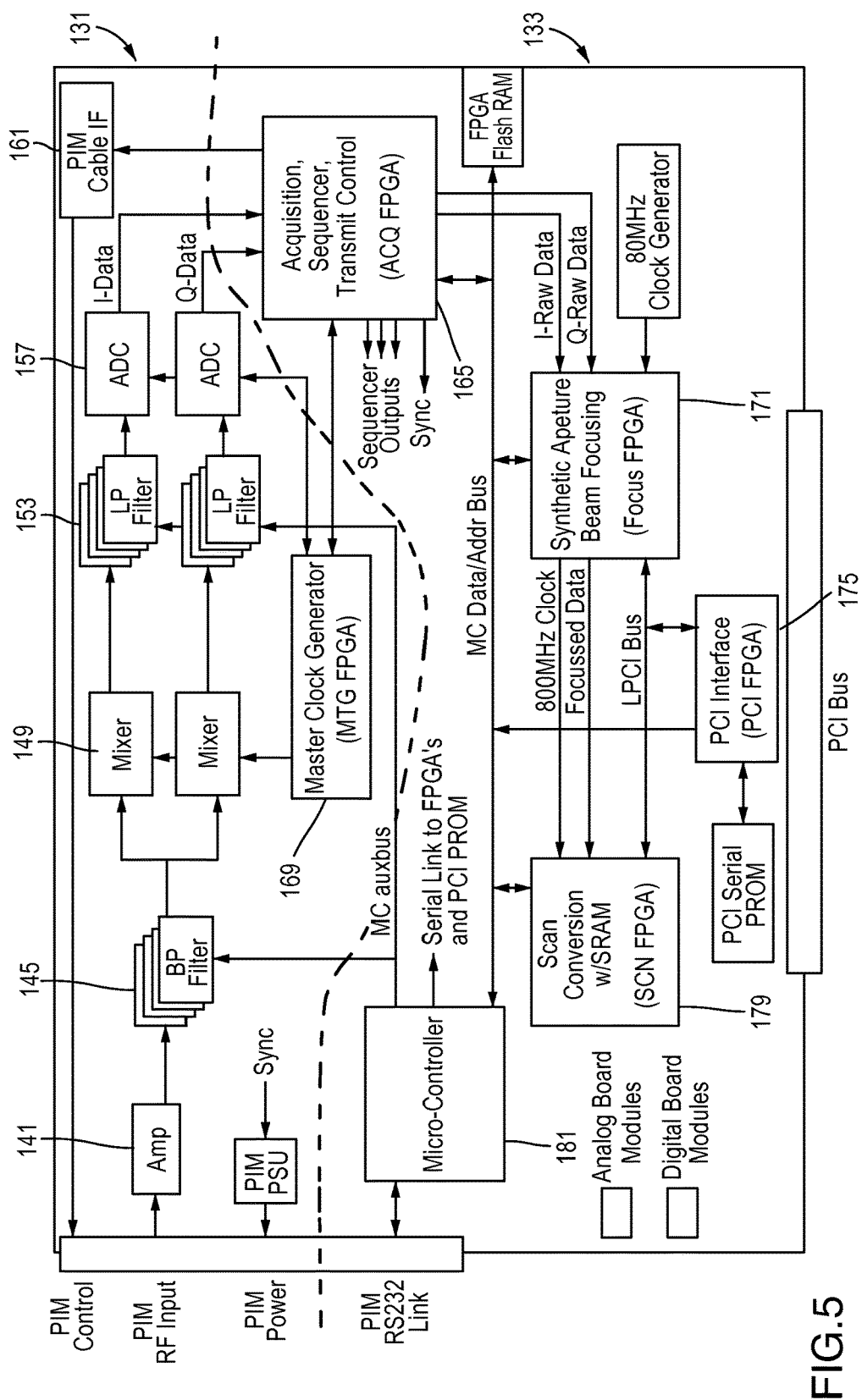
FIG. 5 diagrams a circuit board of the system.

FIG. 5 provides a schematic of analog PCA 131 and digital PCA 133 according to certain embodiments of the invention. Analog PCA 131 is shown to include amplifier 141, band pass filter 145, mixer 149, low pass filter 153, and analog-to-digital converter (ADC) 157. (Here, the system is depicted as being operable to convert the transducer RF data to "In-Phase" and "Quadrature" (IQ) data. According to this embodiment, ADC 157 is 12-bits wide and converts the IQ data to a dual digital data stream.) Analog board 131 further includes an interface module 161 for PIM 105, as well as a clock device 169.

Digital PCA 133 is depicted as having an acquisition FPGA 165, as well as a focus FPGA 171, and a scan conversion FPGA 179. Focus FPGA 171 provides the synthetic aperture signal processing and scan conversion FPGA 179 provides the final scan conversion of the transducer vector data to Cartesian coordinates suitable for display via a standard computer graphics card on monitor 103. Digital board 133 further optionally includes a safety microcontroller 181, operable to shut down PIM 105 as a failsafe mechanism. Preferably, digital PCA 133 further includes a PCI interface chip 175. It will be appreciated that this provides but one exemplary illustrative embodiment and that one or skill in the art will recognize that variant and alternative arrangements may perform the functions described herein. Clock device 169 and acquisition FPGA 165 operate in synchronization to control the transmission of acquisition sequences.

In certain aspects, clock device 169 provides a source of trigger signals and acquisition FPGA 165 triggers firing sequences that collect scan lines of data.

Figure 6:
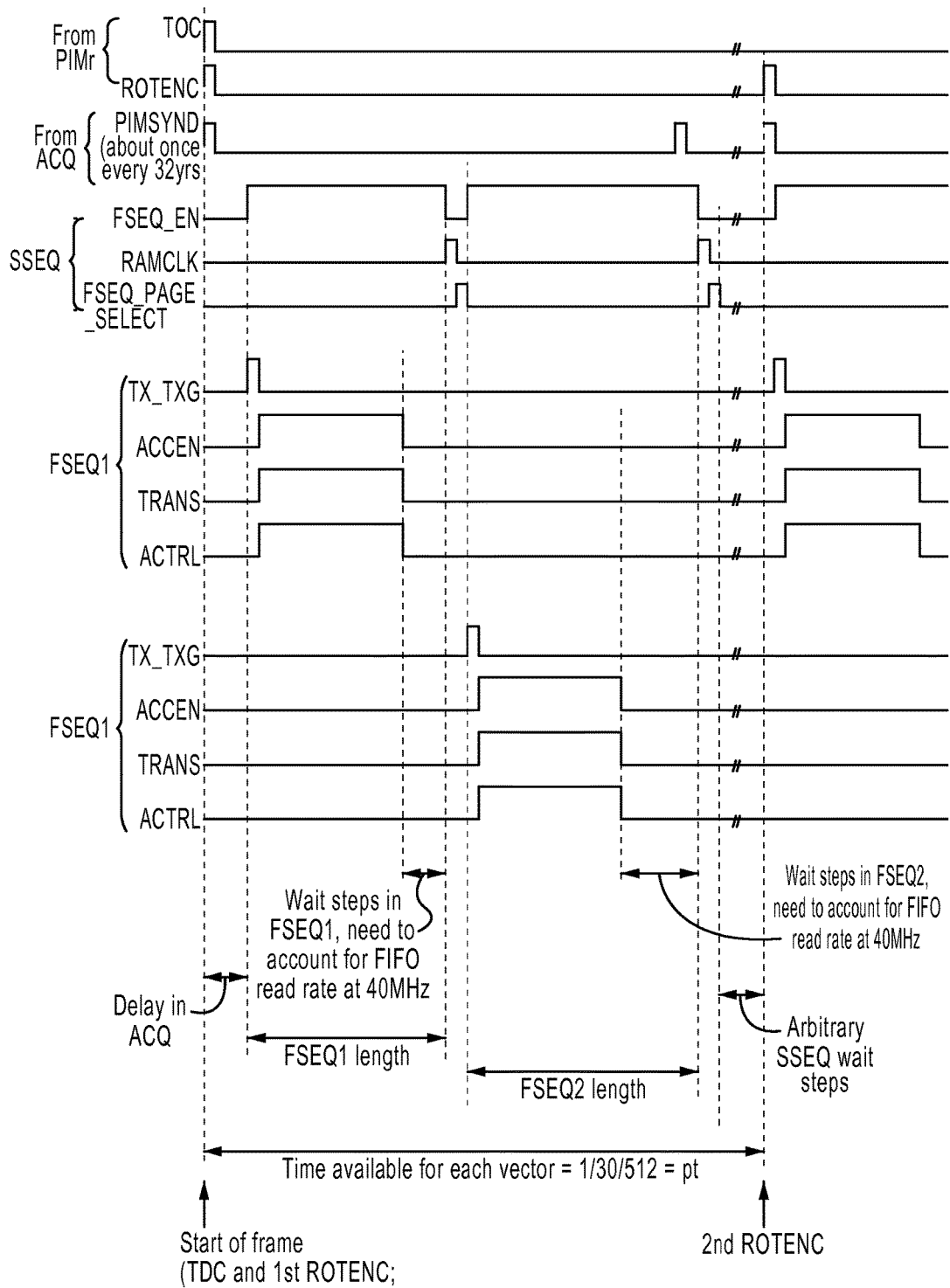
FIG. 6 shows a relationship among signals of components of the invention.

FIG. 6 describes events that may happen in synchrony under coordination of system 101. As shown in FIG. 6, the horizontal axis represents time, while vertical space is used to depict different things that occur simultaneously. Clock device 169 provides a series of trigger signals, here labeled "ROTENC". A processor such as acquisition FPGA 165 uses a module, here labeled SSEQ, to call firing sequencers. Two firing sequencers are depicted, here labeled FSEQ1 and FSEQ2, respectively. Each firing sequence (FSEQ) includes an operation that begins by sending a transmit trigger (here labeled TX_TRIG). The transmit trigger (e.g., a signal sent by acquisition FPGA 165) causes transducer 114 to be excited by an analog impulse and thus to interrogate the patient's tissue with an ultrasonic pulse. Each sequencer operation may typically include acquisition commands (shown as ACQEN, TRANS, and ACTRL) that follow the transmit trigger (although alternative sequencer operations, discussed below, may be performed). Thus, each set of acquisition commands within the sequencer operations provides new lines of data to system 101.

It will be noted that FIG. 6 depicts signal forms as binary states over time (e.g., of a type capable of being sent by devices such as rotary encoders), and the combination of signals can be used (e.g., by acquisition FPGA 165) to order the progression of sequencer operations. For example, FSEQ1 can be ordered to occur only after SSEQ has gone high and ROTENC has been high at least once. FSEQ2 can depend on SSEQ going high a second time, which can be programmed to occur after a wait step after FSEQ1's acquisition commands go low.

The preferred timing of the commands may relate to the operational properties of imaging catheter 112 as well as to the properties of sound. In typical intravascular imaging operations, one "frame" generally refers to one set of data that provides a cross-sectional view of the artery. A catheter that rotates at 1800 RPM makes 30 complete rotations per second. Thus, each frame of data is collected in one thirtieth of a second. Existing, prior art systems used a clock device to provide a fixed number of event triggers for each frame of data acquisition. Prior art systems used the event triggers to fire a ultrasonic impulse and capture a line of data.

Some systems use rotary encoders. Rotary encoders include one or more conductive or optical rings that are encoded around the perimeter with a binary on/off state. For example, a conductive encoder may include copper on half of the ring and plastic on another half. An optical encoder may include an opaque disk with punch-outs that allow an optical signal to go across. Since each ring could encode binary information (on or off; conductive or not; light or dark), and since rotary encoder include a plurality of rings, the number of steps around a full rotation that a rotary encoder can detect is a power of two. The simplest rotary encoder may have two or four steps. Rotary encoders with, for example, 512 or 1024 steps are used. One step of a rotary encoder represents the smallest angular offset that the encoder is physically capable of discriminating. Thus, for example, a 512 step rotary encoder mounted on an imaging catheter is only capable of providing a unique signal, or event trigger, for each 360/512 degrees of rotation (e.g., 0.703 degrees/step). In prior art imaging systems, the number of event triggers from the clock device 169 defines the line density of each image scan. If the system included a 512 step rotary encoder, the system produced 512 lines per frame of image data. Additionally, it is understood that rotary encoders with too many steps do not provide reliable fidelity in imaging systems.

Here, as shown in FIG. 6, systems and methods of the invention provide a sequencer operation performed by a processor that uses a trigger event from clock device 169 to trigger more than one sequencer operation and thus fire more than one ultrasound pulse into tissue for each trigger from the clock.

In some embodiments, increasing the line density includes adjusting the scan depth. For example, if catheter 112 rotates 30×per second, then each rotation requires (1/30) seconds, or 0.0333 seconds. If transducer 114 transmits an ultrasonic pulse at a baseline frequency of 512 per each rotation, then the transmissions will be separated by a baseline period of (0.0333/512) seconds, or about 65 microseconds (µs). If the speed of sound in blood and tissue is taken to be 1,560 m/s—or 1.56 mm/µs—then each ultrasonic pulse will be able to travel a distance, by d=rt, of 1.56 mm/µs×65 µs, which gives about 100 mm. Given that ultrasonic imaging requires the sound to make a round trip, and given that the hardware requires a little bit of time for transmitting the electronic signal and coordinating the operations, the exemplary system would be able to image to a baseline depth of almost about 50 mm, e.g., about 30 to about 40 mm. In certain embodiments, doubling the line density halves the time between transmissions (i.e., 2×frequency→0.5×period) and allows scanning to about half the baseline depth, e.g., to about 15 to about 20 mm. However, doubling the scan line density can greatly improve image quality by increasing resolution, decreasing signal-to-noise ratio (SNR), or a combination thereof.

In some embodiments, scanning depth is not limited and a computer processor (e.g., acquisition FPGA 165) receives backscattered ultrasound impulses from the immediately previous transmission as well as from one or more prior transmission and decodes the overlapping or interfering signals using, e.g., interferometric processing techniques such as fast Fourier transform. Additionally or alternatively, in other embodiments such as those discussed below, system 101 is operated such that a firing sequence operation includes operations other than just one transmit and one receive per firing sequence operation.

Figure 7:
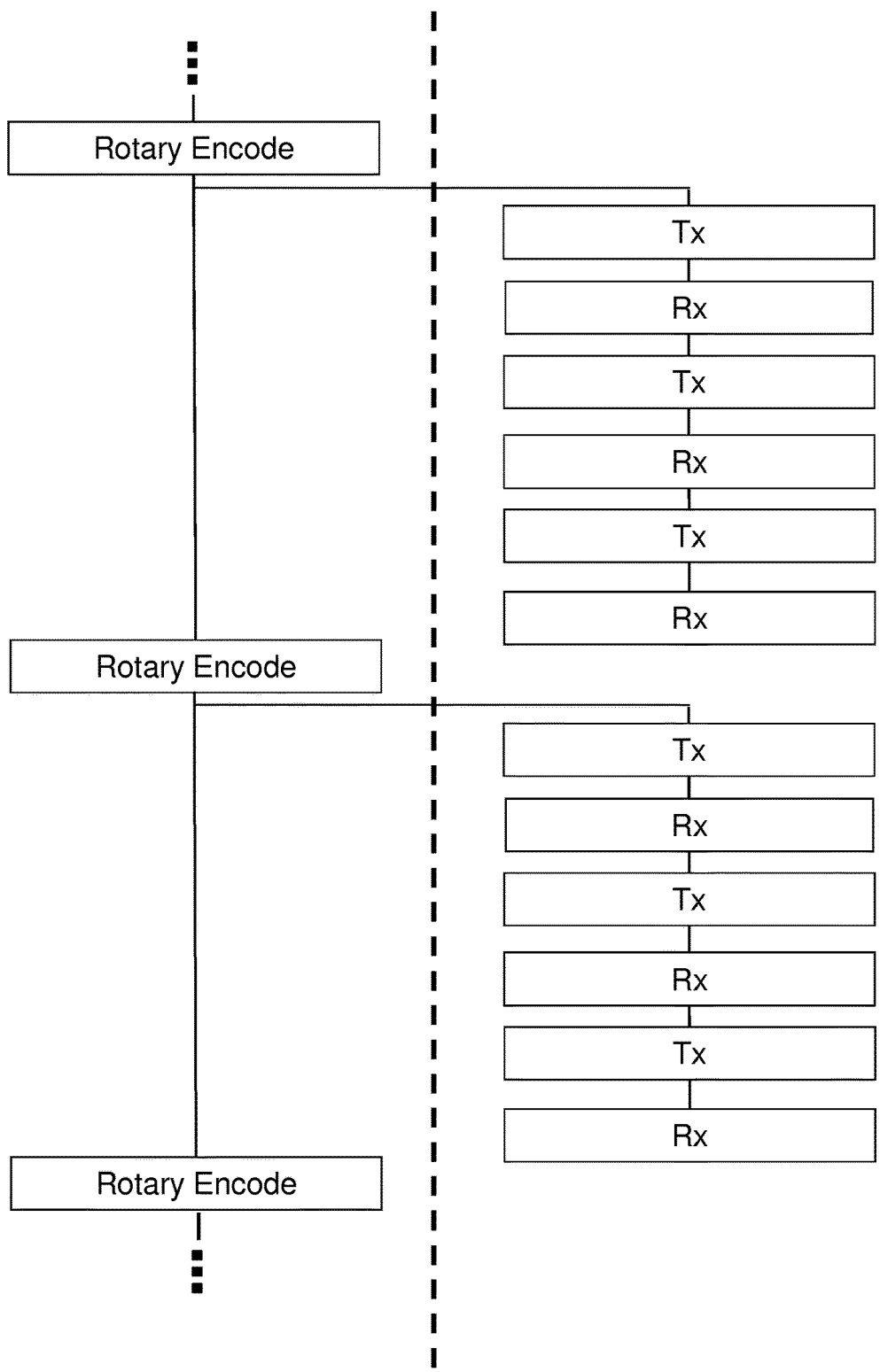
FIG. 7 diagrams a sequence of events according to certain embodiments.

FIG. 7 provides a high-level block diagram of use of system 101 to trigger a plurality of sequencer operations for each of a plurality of trigger operations. As shown in FIG. 7, clock device 169 issues a firing trigger periodically. For example, if clock device 169 is a 512-step rotary encoder and catheter 112 of system 101 rotates at 1800 RPM, then each trigger will be a rotary encode separated by a period of about 65 µs. In this illustrative example, the period of a rotary encoder step is the minimum amount of catheter rotation that the system is capable of physically coordinating a signal with through the use of clock device 169. Acquisition FPGA 165 responds to each trigger signal by firing three firing sequences. Each firing sequence includes a transmit (Tx) trigger and a receive (Rx) trigger. Each transmit trigger causes transducer 114 to issue a pulse of ultrasonic energy and each receive trigger causes transducer 114 to operate for a period (e.g., about ⅙ of 65 µs) to receive backscattered ultrasonic signals and relay those received signals to focus FPGA 171. Here, each rotary encode is depicted as resulting in three firing sequencer operations. However, other operations are provided.

Figure 8:
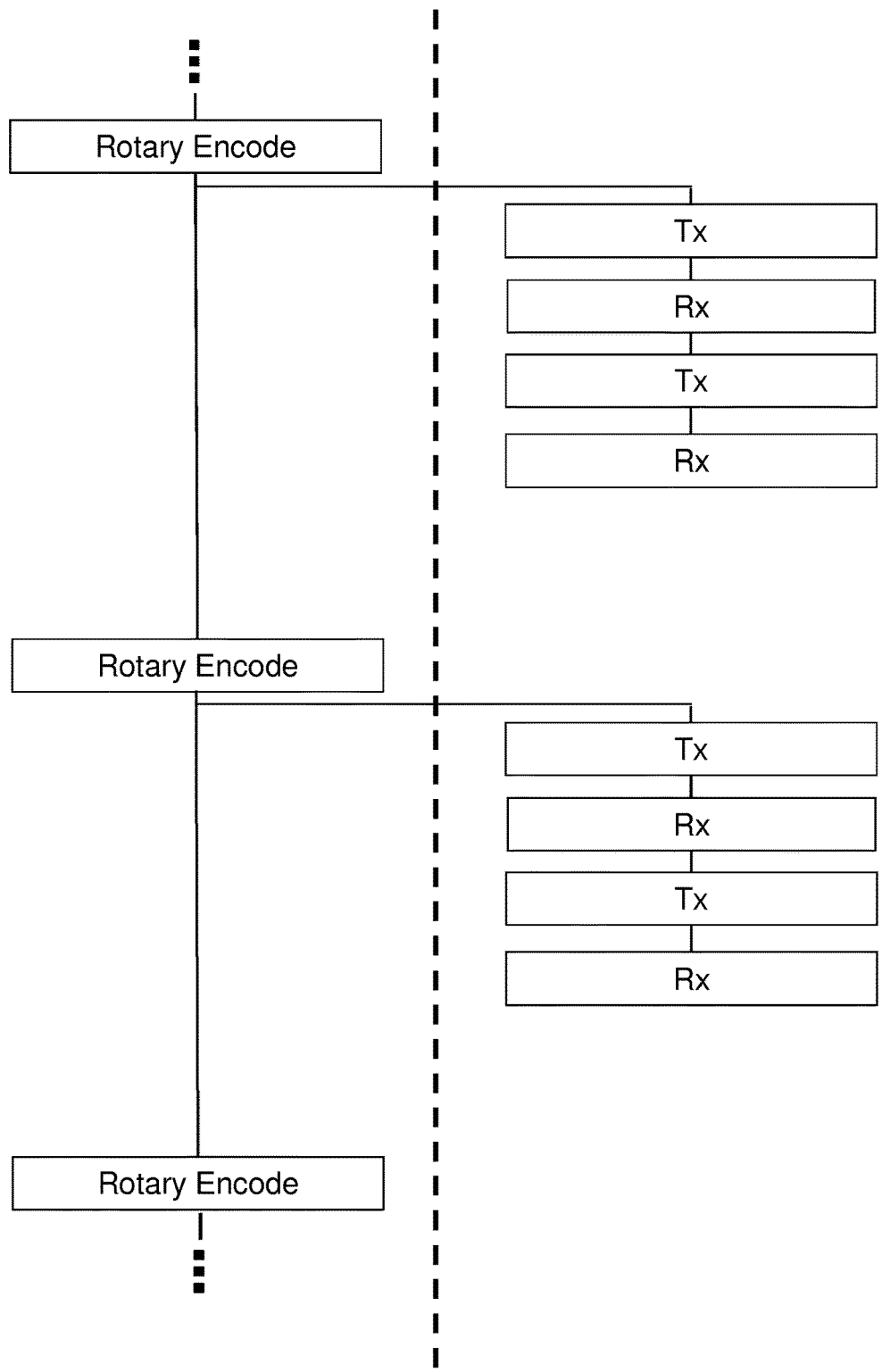
FIG. 8 diagrams capturing two lines per encode according to certain embodiments.

FIG. 8 illustrates use of a clock device 169 to provide two sequencer operations for each firing trigger. As shown in FIG. 8, each sequencer operation includes a transmit (Tx) trigger and a receive (Rx) trigger, as discussed above.

Figure 9:
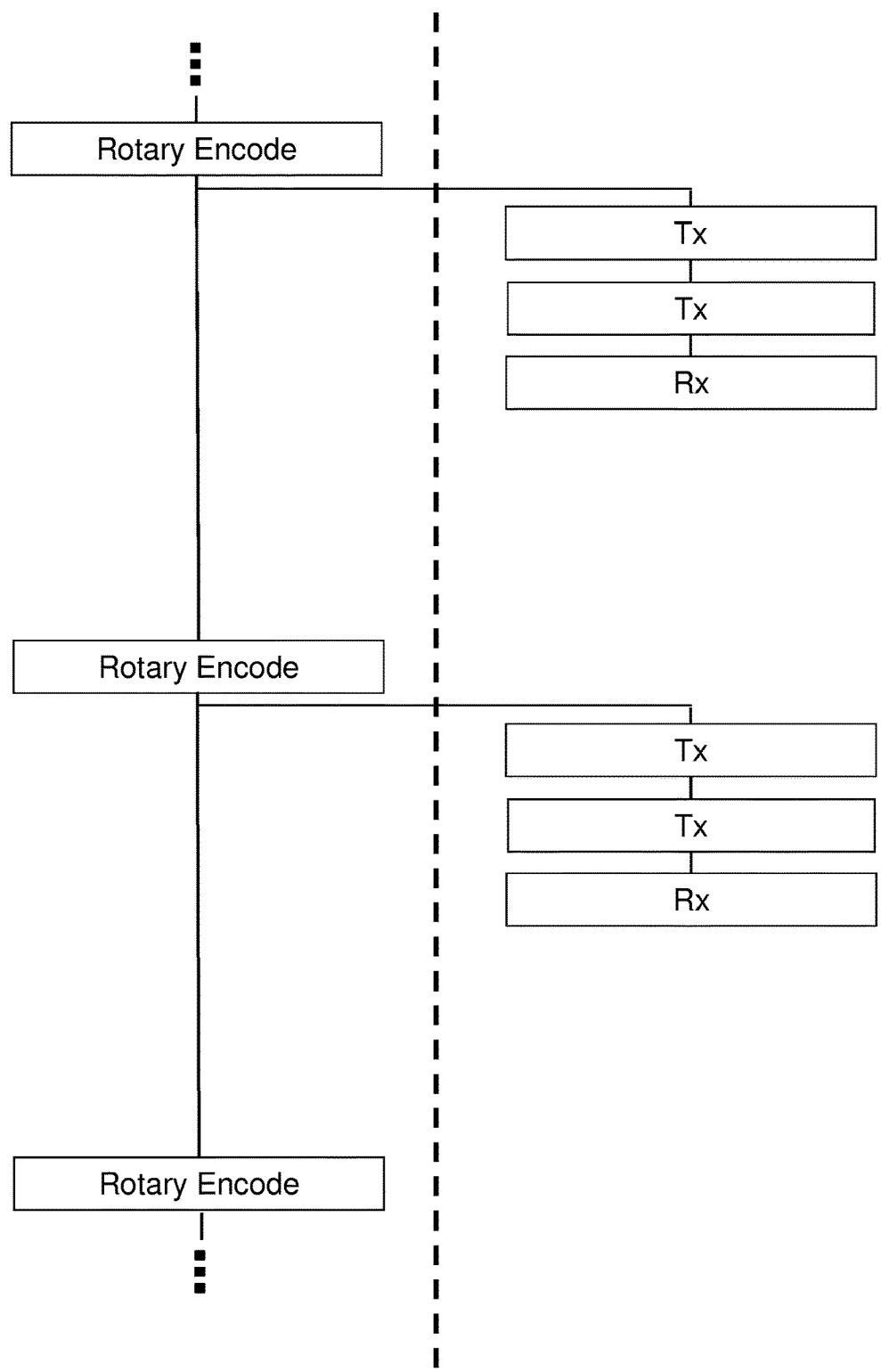
FIG. 9 diagrams a sequence for harmonic imaging according to certain embodiments.

FIG. 9 shows a pattern of use of system 101 for harmonic imaging. As shown in FIG. 9, each rotary encode causes first one transmission, then another, followed by a receipt. Here, the adjacent transmissions may include sound at harmonic frequencies. For example, a first Tx may define one frequency, and the subsequent Tx may include sound at the first harmonic of the one frequency. Through this methodology, tissue can be examined at higher order frequencies.

FIG. 9 also illustrates a pattern of use for pulse inversion imaging. Pulse inversion imaging could be used to boost the image signal and improve resolution. Each transmit could be at the same frequency, but the first begins with a positive amplitude and the second begins the a negative (e.g., in phase or not). Thus a transducer 114 could be used to send a pulse train, and the received signal (at Rx) will be based on the whole train. For neighboring acquisitions, different pulse trains can be used, and those can be added or averaged (e.g., at focus FPGA 171).

Figure 10:
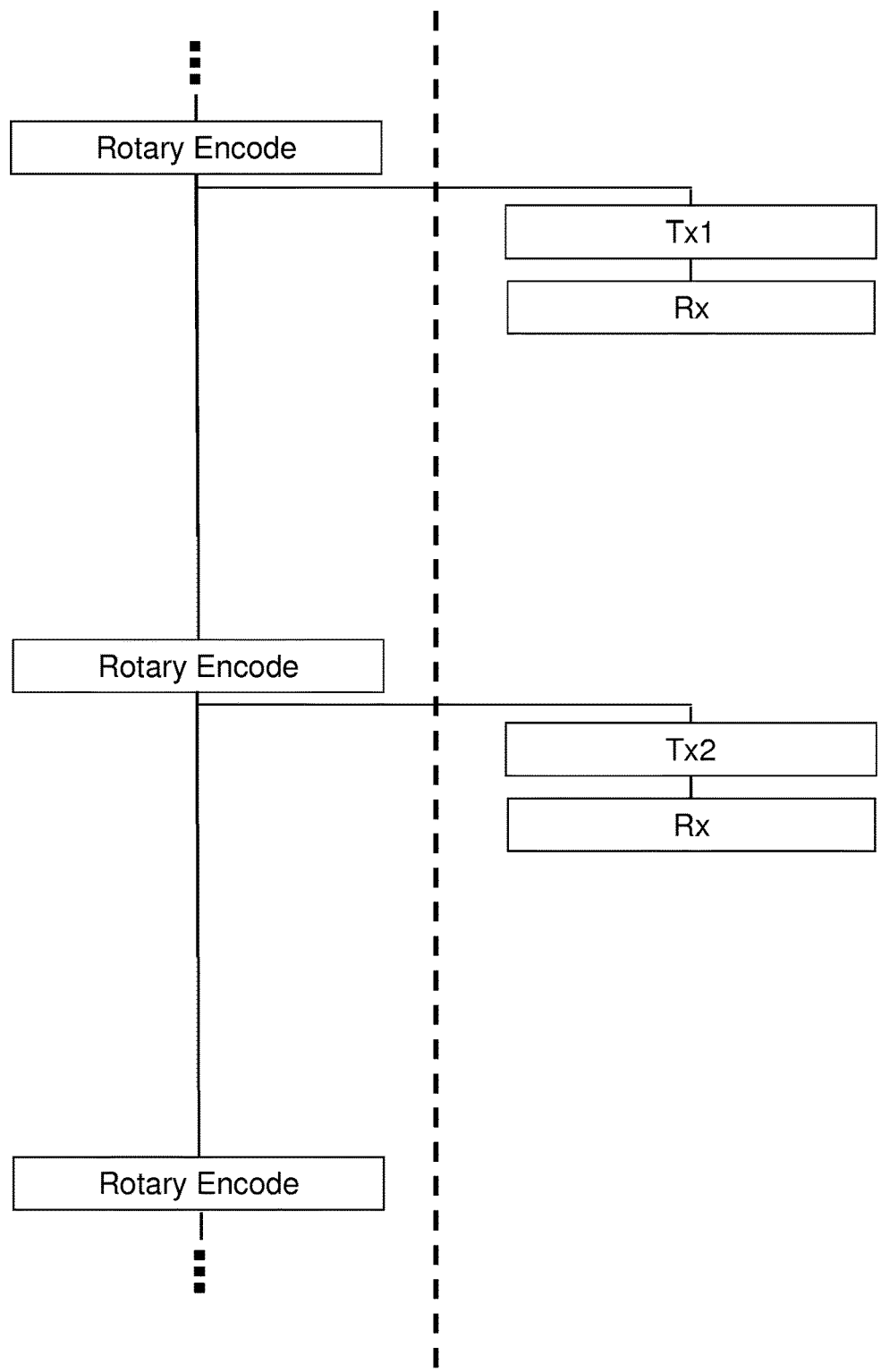
FIG. 10 shows a sequence for interleaved imaging.

FIG. 10 illustrates use of system 101 for interleaved imaging. Here, each trigger signal is used to trigger a firing sequencer operation that is different than the prior firing sequencer operation. In one embodiment, this provides A lines that alternate in frequency. For example, if every other A line is at 20 Hz with the rest being at 60 Hz, the different frequencies can be used simultaneously to easily discern both the luminal border (e.g., the blood/tissue boundary) and the medial-adventital border (e.g., defining a perimeter of an adverse plaque). Accordingly, operating system 101 according to a pattern described by FIG. 10 can provide an estimate of arterial % occlusion in a single IVUS scan.

Figure 11:
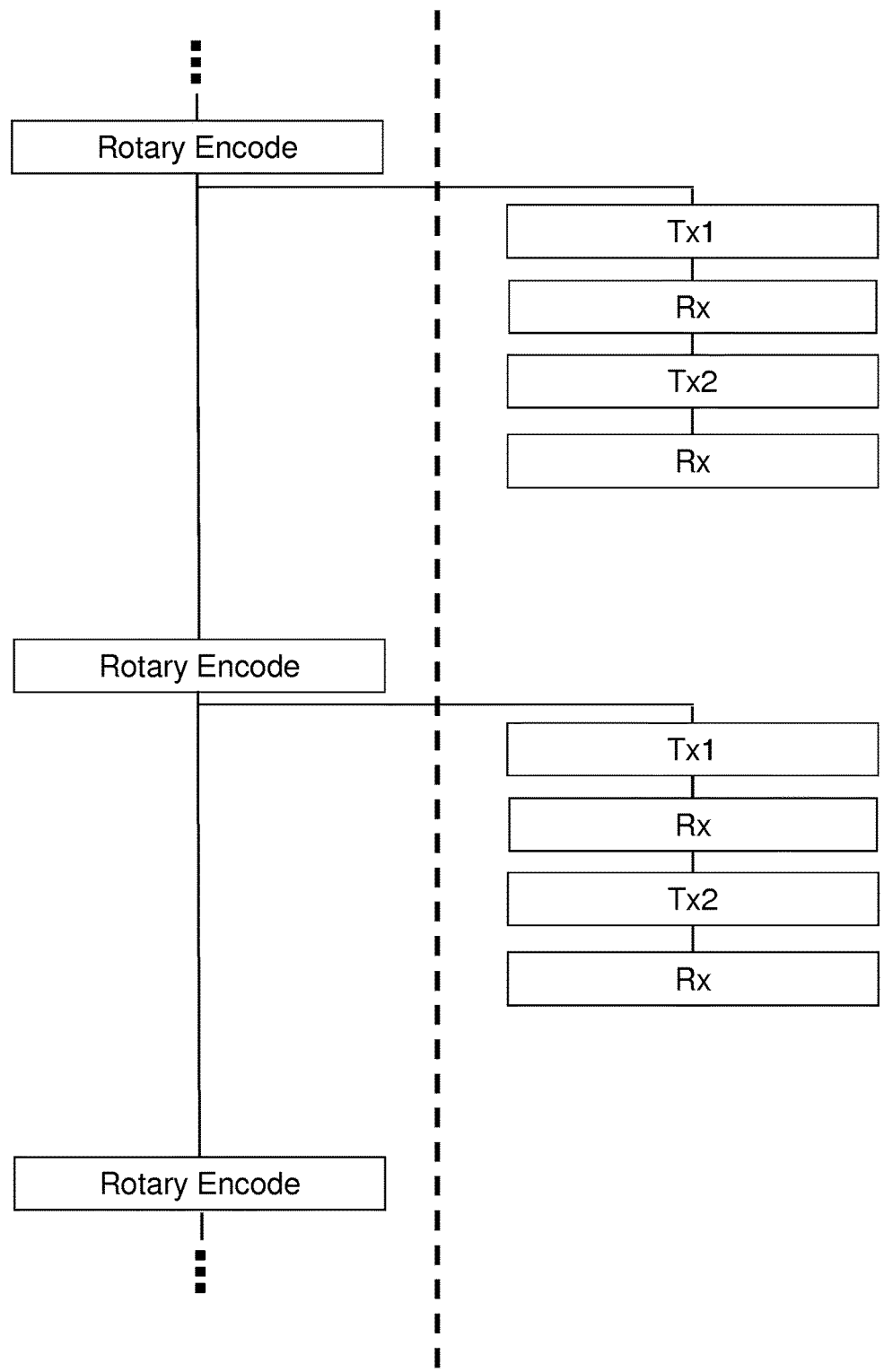
FIG. 11 illustrates firing unlike transmits per each encode.

FIG. 11 depicts an additional or alternative approach to interleaved imaging. Here, each trigger signal is used to fire two sequencing operations, each of which includes a different transmission (e.g., different frequencies as discussed above). Methods and systems of the invention have particular application in increasing IVUS bandwidth as shown, for example, in FIG. 11. Bandwidth refers to a difference between upper and lower cutoff in spectrum (e.g., in MHz). Where a single transmit occurs at, for example, 40 MHz, the full bandwidth may range from about 30 MHz to about 50 MHz If Tx1 and Tx2, as shown in FIG. 11, are at different frequencies, a total bandwidth may be increased. This may have particular application in Doppler imaging, pulsed Doppler, and Doppler-based flow analysis. Doppler flow analysis typically involves sending a pulse in a direction in which velocity is of interest (e.g., along a vessel) and detecting a Doppler shift in the backscatter. Since embodiments of the invention allow for transmissions at multiple frequencies, very sensitive flow velocity profiling may be provided.

Figure 12:
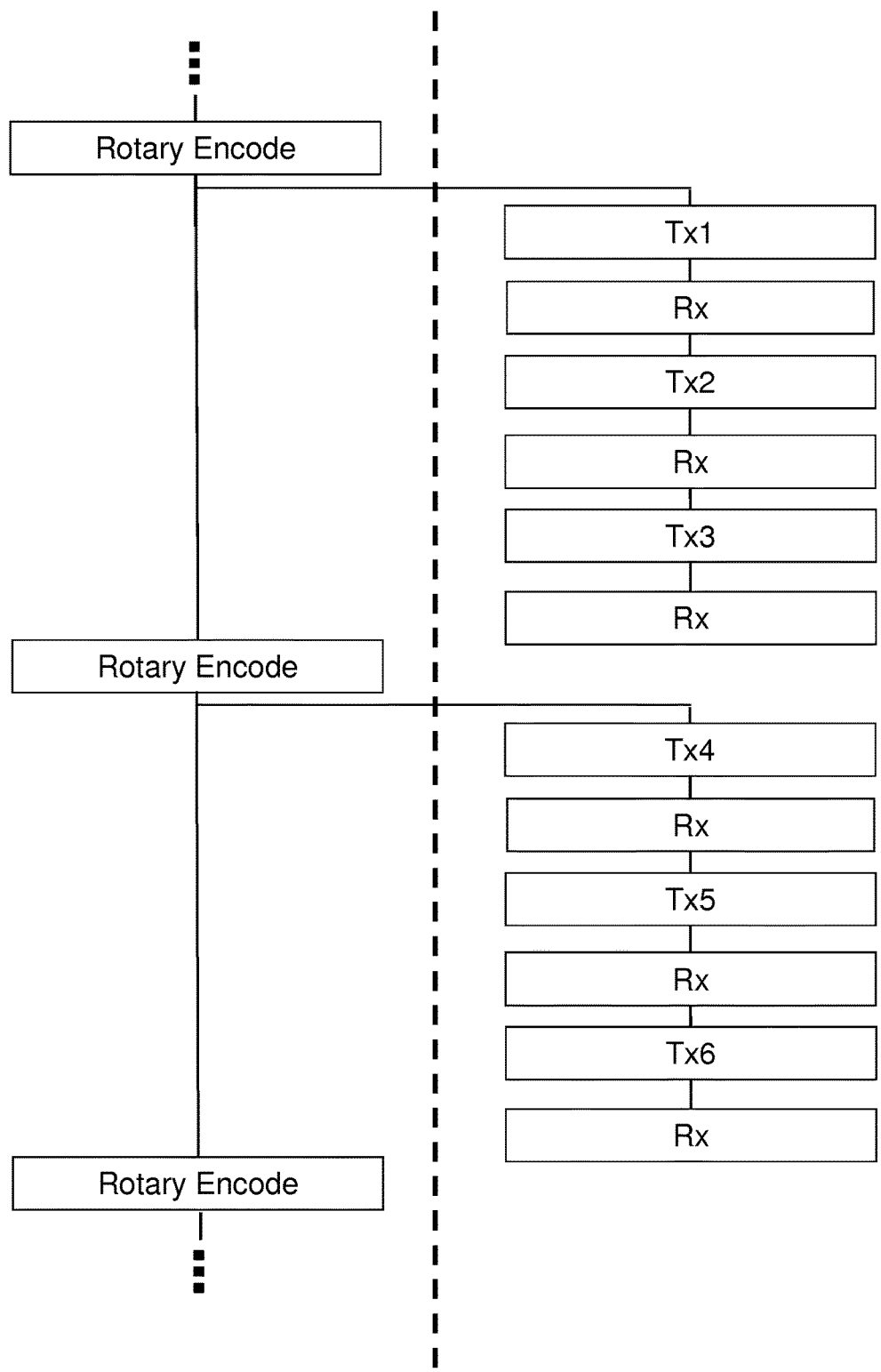
FIG. 12 depicts firing multiple unlike transmits across a plurality of encodes.

FIG. 12 shows an embodiment in which each and every sequencer operation is different than each of the others. This may provide progressive spectrum scanning in which, for example, each A line is operated at an incremented frequency to aid in discovering an optimal frequency for a subsequent operation, to aid in device calibration, or to aid in advanced harmonics research. Embodiments such as the one depicted in FIG. 12 may provide very broad bandwidth IVUS imaging with far-reaching applications in Doppler analysis.

Figure 13:
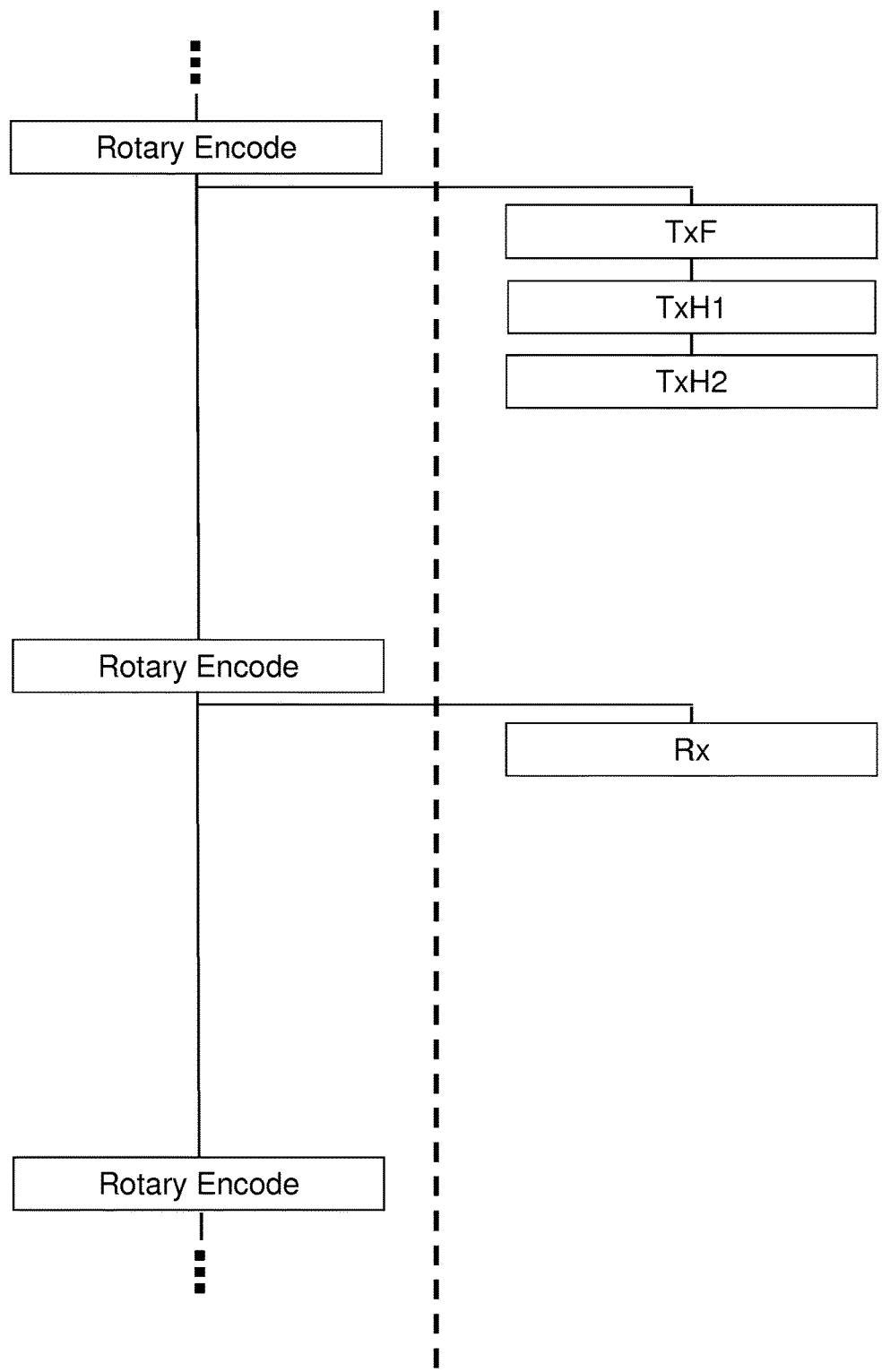
FIG. 13 shows the use of separate encodes for transmit and receipt.

FIG. 13 diagrams an application of systems and methods of the invention to harmonic imaging. Here, each firing trigger is shown being associated with different sequencer operations. The first firing trigger is used to fire three sequencer transmit operations. Each sequencer transmit operation involves exciting transducer 114 with an ultrasonic pulse of a different frequency. As depicted here, the first transmit operation includes an ultrasonic pulse at a frequency that defines a fundamental frequency. The second ultrasonic pulse is transmitted at a harmonic (e.g., the first harmonic) of the fundamental frequency. The third ultrasonic pulse is transmitted at some higher order harmonic of the fundamental frequency. Then, the second firing trigger triggers a firing sequencer operation that comprises primarily a receipt operation, causing transducer 114, catheter 112, and acquisition FPGA 165 to operate to "listen" to the harmonic imaging backscatter signal.

As described above, clock device 169 and acquisition FPGA operate to provide system 101 with a module that drives rotation of catheter 112 while providing a plurality of trigger signals and each trigger signal can be used to trigger various patterns of firing sequencer operations. Systems and methods of the invention provide the ability to have different types of fast sequencer acquisition from one rotational encode to the next or within a rotational encode. In some embodiments, variable sequencer acquisitions allow for harmonic imaging. One important contribution of the inventive systems and methods includes the location of a proximal causes of firing sequencer operations out of clock device 169

(e.g., SSEQ in FIG. 6 can be provided by acquisition FPGA 165, or—in certain embodiments—by a dedicated FPGA not depicted here). This contribution uncouples the pattern of firing sequencers from the rotary encodes. In some embodiments, this is performed by new structure in which proximal triggers to transmit operations come from a timing element within a microprocessor in reaction to a timing signal from a clock device. For example, if the rotary encode period is 65 µs, despite some overall non-uniform rotational velocity of catheter 112, the rotary encode period provides a foundation of timing accuracy and the microprocessor timing element will perform operations with position-time precision. For example, if a microprocessor timing element causes a first step to occur at each rotary encode and a second step to occur 32.5 µs after each rotary encode, then even a non-uniform rotational velocity of catheter 112 will not interfere with fidelity of a set of scan lines (e.g., even if catheter 112 rotates at ±25% of an intended 1800 RPM with a 512 step rotary encoder, then the steps timed by the microprocessor timing element will provide scan lines that are, at most, 0.53° displaced). Since the microprocessor timing is handled on-chip, the system provides the benefit that components can be independently upgraded. For example, if a field-deployed system is to be later changed by replacing any of the processors (e.g., as depicted in FIG. 5), the new processor needs simply to be programmed in accordance with the microprocessor timing element. Moreover, if a manufacturer is to change a product line (e.g., introduce the use of an accelerated processor in digital PCA 133), since the timing methods described herein can be handled on-chip, a full suite of new hardware components need not be introduced. In fact, the systems and methods of the invention are suited for increasing line density in an existing system without replacing a timing device 169 and may be beneficially and conveniently implemented during servicing or replacement of a processor.

As used herein, the word "or" means "and or or", sometimes seen or referred to as "and/or", unless indicated otherwise.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

What is claimed is:

1. A method for intravascular imaging, the method comprising:
   introducing an ultrasonic transducer into a vessel, the transducer being disposed at a distal portion of a catheter;
   using a module operably coupled to a proximal portion of the catheter to provide a number of trigger signals per rotation of the ultrasonic transducer, the module comprising a rotary encoder comprising hardware steps configured to define the number of trigger signals;
   rotating the ultrasonic transducer at least one rotation; and
   triggering a first sequencer operation and a second sequencer operation with each trigger signal,
      wherein the first sequencer operation and the second sequencer operation each comprise stimulating the ultrasonic transducer to transmit an ultrasonic signal into the vessel;
      wherein at least the second sequencer operation comprises receiving a backscattered ultrasound signal from the vessel with the ultrasonic transducer.

2. The method of claim 1, wherein the first sequencer operation comprises ultrasonic imaging at a first frequency and the second sequencer operation comprises ultrasonic imaging at a second frequency.

3. The method of claim 1, wherein the first sequencer operation consists of sending an ultrasonic signal into the vessel and the second sequencer operation comprises sending and receiving a second ultrasonic signal.

4. The method of claim 1, wherein the first sequencer operation comprises acquiring a scanline with a short pulse and the second sequencer operation comprises acquiring a scanline with a long pulse.

5. The method of claim 1, further comprising capturing a number of A lines of ultrasound data per rotation of the ultrasonic transducer greater than the number of trigger signals.

6. An intravascular imaging system comprising:
   a catheter with an ultrasonic transducer;
   a rotary encoder coupled to the catheter comprising a number of hardware steps and configured to produce a plurality of rotary encodes per each 360° rotation of the catheter corresponding to the number of hardware steps; and
   a processor in communication with the rotary encoder and configured to cause the ultrasonic transducer to transmit an ultrasonic pulse at a fundamental frequency and an ultrasonic pulse at a harmonic of the fundamental frequency and receive a backscattered ultrasound signal in response to each rotary encode of the plurality of rotary encodes.

7. A system for intravascular imaging, the system comprising:
   an ultrasonic transducer disposed at a distal portion of an intravascular imaging instrument;
   a module operably coupled to a proximal portion of the intravascular imaging instrument, the module configured to provide a number of trigger signals per rotation of the ultrasonic transducer, the module comprising a rotary encoder comprising hardware steps configured to define the number of trigger signals; and
   a processor configured to trigger a first sequencer operation and a second sequencer operation in response to each trigger signal,
      wherein the first sequencer operation and the second sequencer operation each comprise stimulating the transducer to transmit an ultrasonic signal into a vessel,
      wherein at least the second sequencer operation further comprises receiving a backscattered ultrasound signal from the vessel with the ultrasonic transducer.

8. The system of claim 7, wherein the first sequencer operation comprises ultrasonic imaging at a first frequency and the second sequencer operation comprises ultrasonic imaging at a second frequency.

9. The system of claim 7, wherein the first sequencer operation consists of sending an ultrasonic signal into the vessel and the second sequencer operation comprises sending and receiving a second ultrasonic signal.

10. The system of claim 7, wherein the first sequencer operation comprises acquiring a scanline with a short pulse and the second sequencer operation comprises acquiring a scanline with a long pulse.

11. The system of claim 7, wherein the first sequencer operation and the second sequencer operation each comprise capturing A-line data, and the processor is configured to average the A-line data of the first sequencer operation and the second sequencer operation.

12. The system of claim 7, wherein the ultrasonic signals of the first sequencer operation and the second sequencer operation are the same frequency, and wherein the ultrasonic signal of the second sequencer operation is the inverse of the ultrasonic signal of the first sequencer operation.

13. The system of claim 7, wherein the first sequencer operation and second sequencer operation each comprise using the ultrasonic transducer to receive a backscattered signal from the vessel.

14. The system of claim 13, wherein the ultrasound signal of the first sequencer operation has a first frequency and the ultrasound signal of the second sequencer operation has a second frequency that is different from the second frequency.

15. The system of claim 14, wherein the ultrasound signal of the first sequencer operation has a first bandwidth and the ultrasound signal of the second sequencer operation has a second bandwidth, and wherein the second bandwidth at least partially overlaps the first bandwidth.

16. The system of claim 13, wherein the processor is operable to:
    trigger the first sequencer operation and the second sequencer operation by a first trigger signal of the number of trigger signals; and
    trigger a third sequencer operation and a fourth sequencer operation by a second trigger signal of the number of trigger signals,
    wherein the third and fourth sequencer operations each comprise stimulating the transducer to transmit an ultrasonic signal into the vessel, and wherein the ultrasonic signals of the first, second, third, and fourth sequencer operations have different frequencies.

\* \* \* \* \*